US010675476B2

(12) United States Patent
Reddy et al.

(10) Patent No.: US 10,675,476 B2
(45) Date of Patent: Jun. 9, 2020

(54) INTERNAL THORACIC VEIN PLACEMENT OF A TRANSMITTER ELECTRODE FOR LEADLESS STIMULATION OF THE HEART

(71) Applicant: CARDIAC PACEMAKERS, INC., St. Paul, MN (US)

(72) Inventors: G. Shantanu Reddy, Minneapolis, MN (US); Kenneth Martin Stein, Minneapolis, MN (US); John Morgan, Houghyon (GB)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 220 days.

(21) Appl. No.: 15/847,435

(22) Filed: Dec. 19, 2017

(65) Prior Publication Data

US 2018/0178018 A1    Jun. 28, 2018

Related U.S. Application Data

(60) Provisional application No. 62/438,299, filed on Dec. 22, 2016.

(51) Int. Cl.
*A61N 1/378* (2006.01)
*A61N 1/372* (2006.01)
*A61N 1/375* (2006.01)
*A61N 1/05* (2006.01)

(52) U.S. Cl.
CPC ....... *A61N 1/3787* (2013.01); *A61N 1/37288* (2013.01); *A61N 1/0563* (2013.01); *A61N 1/3756* (2013.01); *A61N 1/37211* (2013.01); *A61N 1/37512* (2017.08)

(58) Field of Classification Search
CPC ...... A61N 1/36; A61N 1/3606; A61N 1/0563; A61N 1/37288; A61N 1/39622; A61N 1/05; A61N 1/37512; A61N 1/056; A61N 1/08; A61N 1/362; A61N 1/00; A61N 1/0504; A61N 1/36017; A61N 2001/0585; A61B 5/686; A61B 5/0031; A61B 5/4836; A61B 5/6869; A61B 5/042; A61B 5/0051
See application file for complete search history.

(56) References Cited

U.S. PATENT DOCUMENTS

| 3,659,615 A | 5/1972 | Enger |
| 3,735,756 A | 5/1973 | Richards et al. |
| 5,193,539 A | 3/1993 | Schulman et al. |

(Continued)

FOREIGN PATENT DOCUMENTS

| WO | 2016148928 A1 | 9/2016 |
| WO | 2016149262 A1 | 9/2016 |

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — Deborah L Malamud
(74) *Attorney, Agent, or Firm* — Seager, Tufte & Wickhem LLP

(57) ABSTRACT

Implantable medical device systems and methods of use including an implantable first medical device having a lead with a transducer thereon and an implantable second medical device having a receiver for receiving energy emitted by the transducer. The lead may be placed in an internal thoracic vein, and other locations may be used as well. The implantable second medical device may be placed in or on the heart or an associated blood vessel.

20 Claims, 14 Drawing Sheets

(56) References Cited

U.S. PATENT DOCUMENTS

| | | |
|---|---|---|
| 5,331,966 A | 7/1994 | Bennett et al. |
| 6,140,740 A | 10/2000 | Porat et al. |
| 6,504,286 B1 | 1/2003 | Porat et al. |
| 6,628,989 B1 | 9/2003 | Penner et al. |
| 6,647,292 B1 | 11/2003 | Bardy et al. |
| 6,654,638 B1 | 11/2003 | Sweeney |
| 6,721,597 B1 | 4/2004 | Bardy et al. |
| 6,764,446 B2 | 7/2004 | Wolinsky et al. |
| 7,149,575 B2 | 12/2006 | Ostroff et al. |
| 7,177,698 B2 | 2/2007 | Klosterman et al. |
| 7,437,193 B2 | 10/2008 | Parramon et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,890,173 B2 | 2/2011 | Brisken et al. |
| 7,953,493 B2 | 5/2011 | Fowler et al. |
| 7,962,222 B2 | 6/2011 | He et al. |
| 8,005,543 B2 | 8/2011 | Libbus et al. |
| 8,103,359 B2 | 1/2012 | Reddy |
| 8,157,813 B2 | 4/2012 | Ko et al. |
| 8,180,285 B2 | 5/2012 | Rofougaran |
| 8,315,701 B2 | 11/2012 | Cowan et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 9,343,654 B2 | 5/2016 | Moore et al. |
| 9,440,258 B2 | 9/2016 | Klee et al. |
| 9,452,286 B2 | 9/2016 | Cowan et al. |
| 2002/0077673 A1 | 6/2002 | Penner et al. |
| 2004/0172083 A1 | 9/2004 | Penner |
| 2004/0204744 A1 | 10/2004 | Penner et al. |
| 2005/0043765 A1 | 2/2005 | Williams et al. |
| 2012/0029335 A1 | 2/2012 | Sudam et al. |
| 2015/0025612 A1 | 2/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2018/0036527 A1 | 2/2018 | Reddy et al. |
| 2018/0036547 A1 | 2/2018 | Reddy |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Krock et al. |
| 2018/0325480 A1 | 11/2018 | Liu et al. |
| 2018/0344200 A1 | 11/2018 | Thakur et al. |
| 2018/0344252 A1 | 11/2018 | An et al. |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.

Request for Continued Examination (RCE) for U.S. Appl. No. 15/667,167, dated Apr. 10, 2019.

Amendment for U.S. Appl. No. 15/667,221, dated Dec. 21, 2018.
Amendment After Final Office Action for U.S. Appl. No. 15/667,221, dated May 22, 2019.

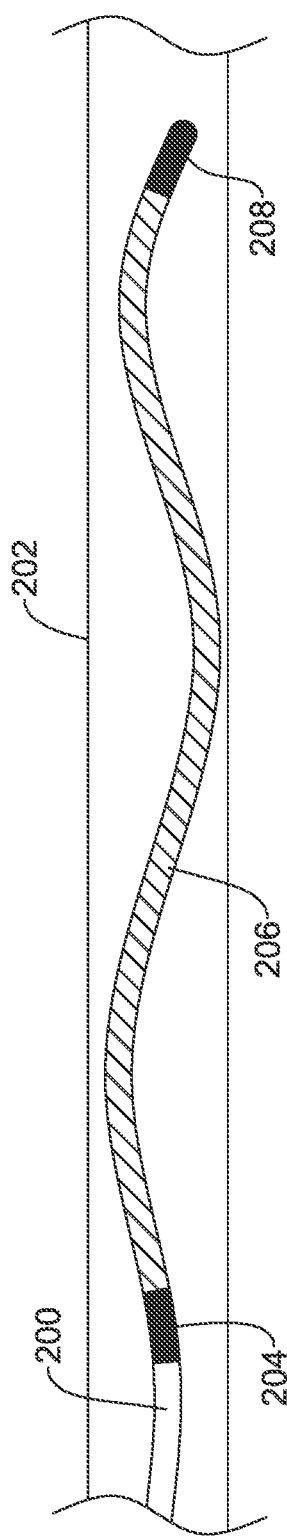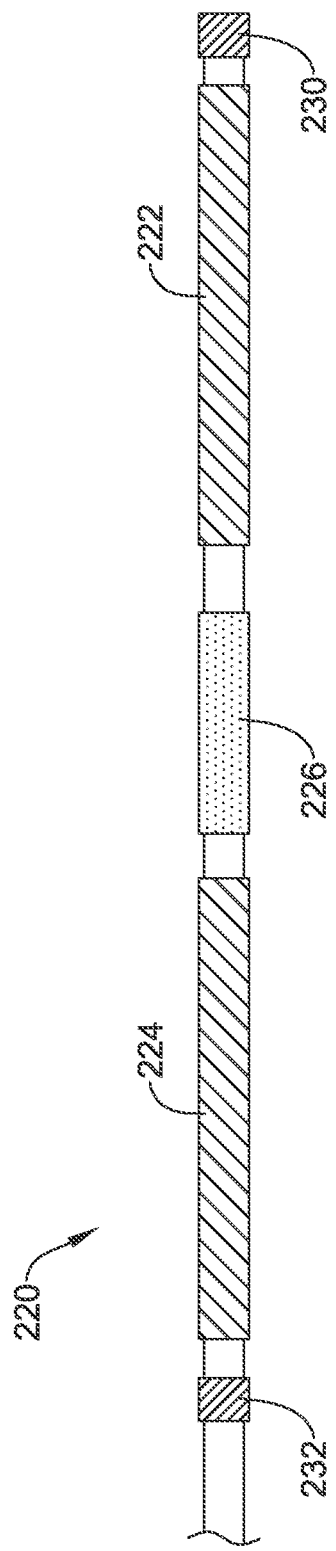

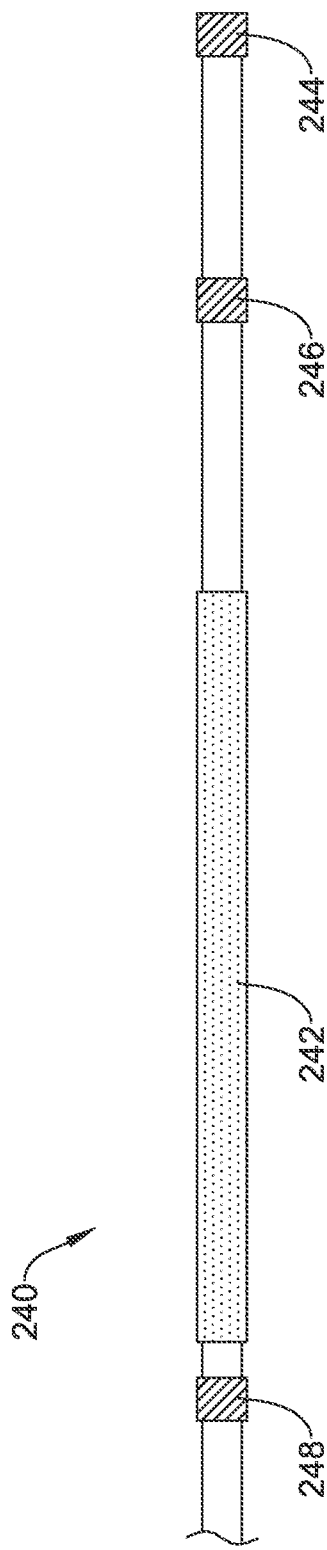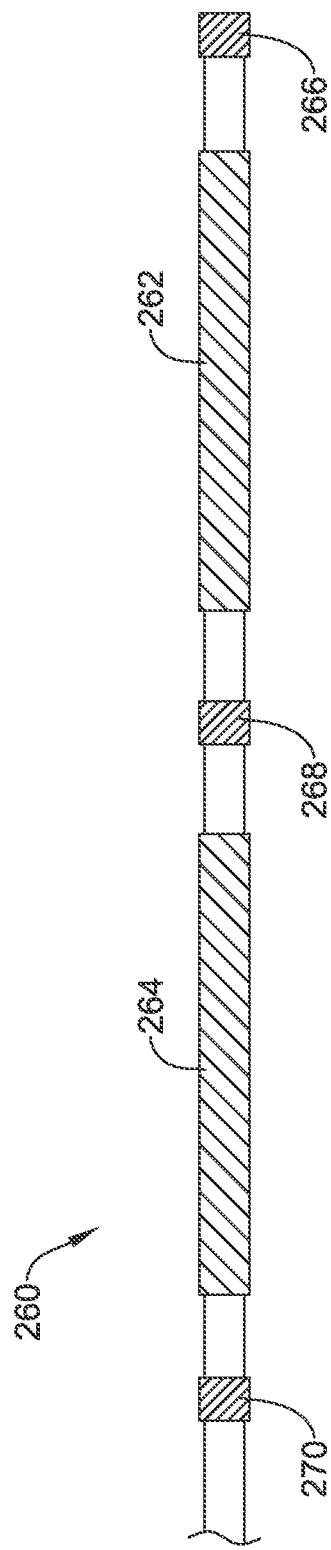

INTERNAL THORACIC VEIN PLACEMENT OF A TRANSMITTER ELECTRODE FOR LEADLESS STIMULATION OF THE HEART

CROSS REFERENCE TO RELATED APPLICATIONS

The present application claims the benefit of and priority to U.S. Provisional Patent Application Ser. No. 62/438,299, filed Dec. 22, 2016, and titled INTERNAL THORACIC VEIN PLACEMENT OF A TRANSMITTER ELECTRODE FOR LEADLESS STIMULATION OF THE HEART, the disclosure of which is incorporated herein by reference.

BACKGROUND

The leadless cardiac pacemaker has the potential to change clinical practice for those patients needing pacing therapy for bradycardia, heart failure (cardiac resynchronization) and/or anti-tachycardia treatments. Generally speaking the idea is to place a leadless device entirely within the heart, a blood vessel of the heart, or on the heart, without having lead attached thereto. Omission of the lead would remove a source of reliability failures (due to lead fracture) and avoid the potential for leads to block blood vessels, interfere with valve function, and act as conduits for infection. Some proposals for leadless cardiac pacemaker systems have suggested receiving power from another implantable device. New and alternative proposals that minimize power loss in the power transfer for such systems are desired.

OVERVIEW

The present inventors have recognized, among other things, that a problem to be solved is the need for more efficient transmission of ultrasound energy to intracardiac ultrasound-powered pacemakers. In some examples, a transducer, such as an ultrasound transmitter, is placed on a lead that resides at least in part in an internal thoracic vein (the right and/or left ITV) which is coupled to an implantable canister. The transducer may stand alone on the lead, or the lead may include one or more sensing or therapy delivery electrodes. In another example, the transducer may be part of a transmitter and defibrillation electrode. The transducer may be used to power one or more stimulators placed in the chambers of the heart, on the outside of the heart, or within one or more of the coronary veins or other blood vessels. In an alternative, the lead having the transducer may extend through one of the brachiocephalic vein or an intercostal vein. In one such example the transducer, alone or as part of a combination transmitter and electrode, may be placed in an intercostal vein. In a still further alternative, the lead may be placed by entering the internal thoracic vein and then exiting the internal thoracic vein to enter the mediastinum, allowing the transducer to be still closer to the heart. One potential benefit of placing the transducer in this manner is that the ribs will not block or attenuate the output mechanical energy, unlike prior systems having a transducer placed over the ribcage.

A first illustrative, non-limiting example takes the form of an implantable medical device system comprising: a first lead comprising a transducer for converting electrical energy to mechanical energy; an implantable first medical device comprising a canister housing operational circuitry for the implantable first medical device, the implantable first medical device configured to couple to the first lead, the operational circuitry including driver circuitry for selectively driving the transducer of the lead; and an implantable second medical device configured for placement in the heart of a patient having a receiver for receiving mechanical energy from the transducer and converting received mechanical energy into electrical energy, and a plurality of electrodes for delivering electrical pacing therapy to the heart of a patient; wherein the first lead is configured for placement in an internal thoracic vein of a patient.

Additionally or alternatively, the first lead may comprise a combination transmitter and defibrillation electrode, of which said transducer is a part, wherein the defibrillation electrode is a coil electrode, and the implantable first medical device may comprise therapy circuitry for delivering a defibrillation therapy using at least the defibrillation electrode of the first lead.

Additionally or alternatively, the first lead may comprise a defibrillation electrode, and the implantable first medical device may comprise therapy circuitry for delivering a defibrillation therapy using at least the defibrillation electrode of the first lead.

Additionally or alternatively, the first lead may comprise at least one pacing electrode for outputting pacing therapy.

Additionally or alternatively, the first lead may comprise a combination transmitter and pacing electrode, of which said transducer is a part.

Additionally or alternatively, the first lead may comprise a plurality of transducers that are separately addressable by the driver circuitry for separately powering a plurality of implantable second medical devices.

Additionally or alternatively, the first implantable medical device may be configured to separately power the plurality of implantable second medical devices by providing output power via the plurality of transducers at a plurality of different transducer frequencies.

Additionally or alternatively, the operational circuitry may comprise sensing circuitry for receiving signals from electrodes disposed on the first lead, on a second lead, or on the canister of the first medical device to detect cardiac function.

Additionally or alternatively, the operational circuitry may be configured to use the sensing circuitry to determine whether a pacing therapy delivered by the second implantable medical device has achieved a desirable outcome, and to adjust the driver circuitry to increase or decrease an amount of power provided by the driver circuitry to the transducer on the lead.

Additionally or alternatively, the operational circuitry may be configured to use the sensing circuitry to determine whether a pacing therapy delivered by the second implantable medical device has achieved a desirable outcome, and to adjust the driver circuitry to modify timing of power provided by the driver circuitry to the transducer on the first lead.

Additionally or alternatively, the transducer of the first lead may be an ultrasound transducer.

Additionally or alternatively, the implantable first medical device may be configured to power and control therapy delivery by the implantable second medical device by: providing power to the second medical device using the transducer on the first lead; and controlling operation of the second medical device by providing a control signal within a power output generated using the transducer.

Additionally or alternatively, the implantable first medical device comprises communication circuitry for communicating to the implantable second medical device separate from the transducer of the first lead, and the implantable first medical device is configured to power and control therapy delivery by the implantable second medical device by: providing power to the second medical device using the transducer on the first lead; and controlling operation of the second medical device by providing a control signal using a communication output generated by the communication circuitry.

Additionally or alternatively, the system may further comprise a second lead, wherein the implantable first medical device comprises a header adapted to receive each of the first and second leads, and further wherein the second lead comprises a transducer for converting electrical energy to mechanical energy, and the driver circuitry is configured to selectively drive the transducer of the first lead and the second lead separately.

A second illustrative, non-limiting example takes the form of a method of treating a patient comprising: generating mechanical energy using a first transducer located on a lead, wherein at least a portion of the lead is located in an internal thoracic vein of the patient; receiving the mechanical energy at a second transducer on an implantable pacemaker located in or on the heart of the patient; converting the mechanical energy to electrical energy in the implantable pacemaker; and generating a therapy output using the electrical energy with the implantable pacemaker.

Additionally or alternatively, the lead may be coupled to an implantable defibrillator comprising a housing containing one or more batteries, sensing circuitry, therapy delivery circuitry, and a driver for the transducer, the lead may further include a defibrillation coil electrode coupled to therapy delivery circuitry located in the housing such that the implantable defibrillator is configured to: deliver defibrillation therapy using the housing and the defibrillation coil in a shocking configuration; and provide power to the leadless pacemaker using the driver and the transducer on the lead.

Additionally or alternatively, the lead may be coupled to an implantable cardiac device comprising a housing containing one or more batteries, sensing circuitry, and a driver for the transducer, such that the implantable cardiac device is configured to: provide power to the leadless pacemaker using the driver and the transducer on the lead; and use the sensing circuitry to determine one or more of an effectiveness of the leadless pacemaker output, a patient cardiac state, or a patient activity level.

Additionally or alternatively, the first transducer may be located in the mediastinal space.

Additionally or alternatively, the first transducer may be located in an intercostal vein connected to the internal thoracic vein.

Additionally or alternatively, the first transducer may be located in the internal thoracic vein.

Additionally or alternatively, the first transducer may be operated at a duty cycle, relative to a 24 hour period, of at least 10%.

Additionally or alternatively, the first transducer may be operated at a duty cycle, relative to a one hour period, of at least 10%.

A third illustrative, non-limiting example takes the form of a method of implanting a medical device system, the medical device system comprising a lead having a mechanical transducer thereon for use in charging a leadless pacemaker and a canister housing a power source and a driver for the transducer, the method comprising: accessing the internal thoracic vessel (ITV) of a patient; inserting at least a portion of the lead in the ITV; coupling the lead to the canister; and implanting the canister.

Additionally or alternatively, the step of inserting at least a portion of the lead in the ITV may include placing the lead such that the transducer resides in the ITV.

Additionally or alternatively, the method may further comprise accessing the mediastinum from the ITV; wherein the step of inserting at least a portion of the lead in the ITV includes placing the lead such that the transducer resides in the mediastinum.

Additionally or alternatively, the method may further comprise advancing at least a portion of the lead in or through an intercostal vein.

Additionally or alternatively, the method may further comprise advancing at least a portion of the lead in or through a brachiocephalic vein.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5-8 show distal ends for a number of illustrative leads;

DETAILED DESCRIPTION

Figure 1:
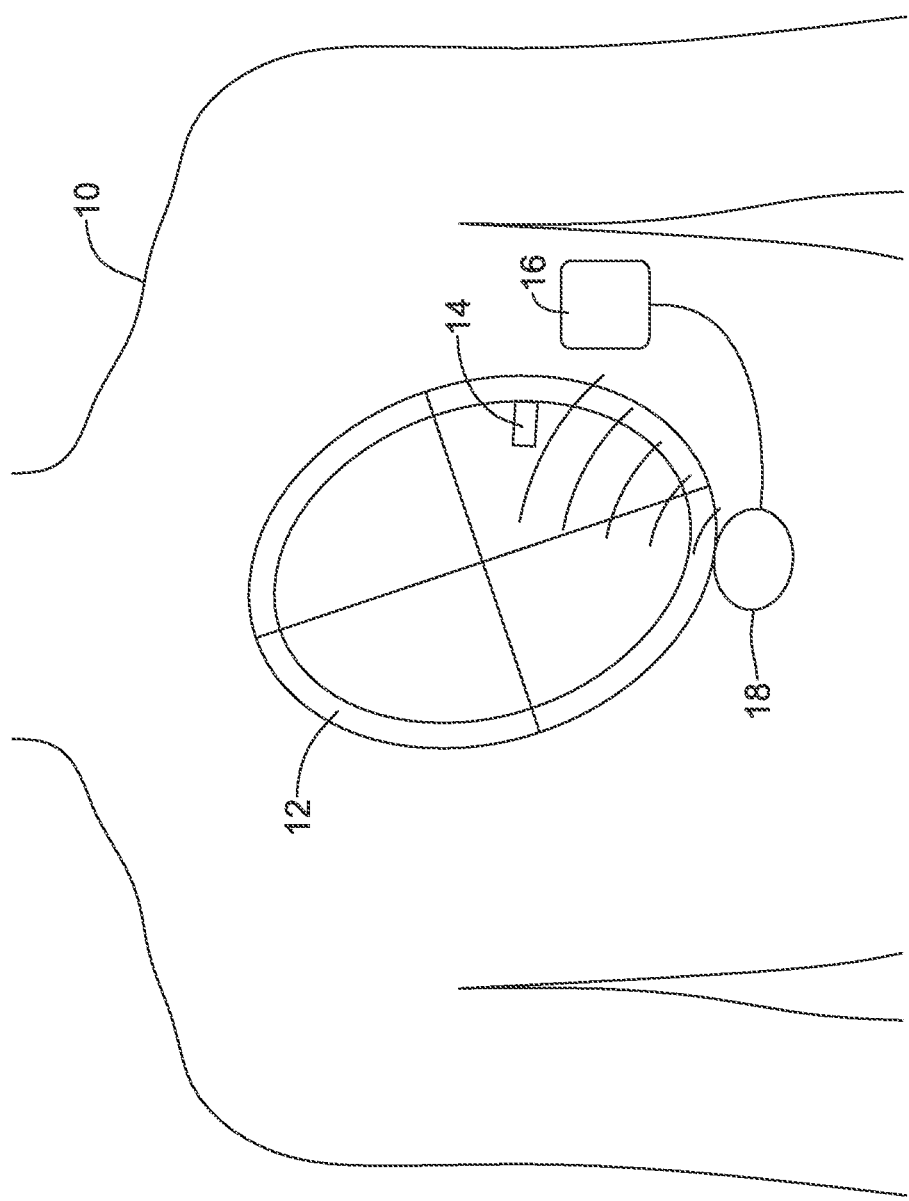
FIG. 1 illustrates a prior art system for providing intracardiac pacing with a subcutaneously placed ultrasound power source.

FIG. 1 illustrates a prior art system for providing intracardiac pacing with a subcutaneously placed ultrasound power source. The system shown generally resembles that of EBR Systems shown, for example, in U.S. Pat. Nos. 7,953, 493 and 8,315,701, and Auricchio et al., FIRST-IN-MAN IMPLANTATION OF LEADLESS ULTRASOUND BASED CARDIAC STIMULATION PACING SYSTEM: NOVEL ENDOCARDIAL LEFT VENTRICULAR RESYNCHRONIZATION THERAPY IN HEART FAILURE PATIENTS, Europace (2013) 15, 1191-1197.

In FIG. 1, the patient 10 with heart 12 has an implantable pacemaker 14 implanted in the left ventricle. The pacemaker 14 comprises a receiver for receiving and converting ultrasound energy into electrical energy, which is then used to deliver pacing therapy output. The ultrasound energy is delivered by a transducer 18 that is coupled to a power supply housing 16. The transducer 18 is placed subcutaneously over the ribs of the patient, on the anterior chest more or less level with the apex of the heart. The power supply housing 16 contains the batteries that supply the energy for the transducer 18, and is generally placed in the left axillar (armpit) of the patient 10.

One concern with the original system as shown is that the batteries in the power supply housing may be short lived. One solution is to make the batteries rechargeable. Another solution is to improve the power transfer from the transducer 18 to the pacemaker 14. The power transfer is limited in part by anatomy, as the ribs are not good conductors of ultrasound energy, and the placement of the transducer 18 over the ribs increases the distance between the transducer 18 and the pacemaker 14. The present invention is directed at alternative designs and placement for the transducer, among other potential benefits that will become apparent in the following detained description.

Figure 2:
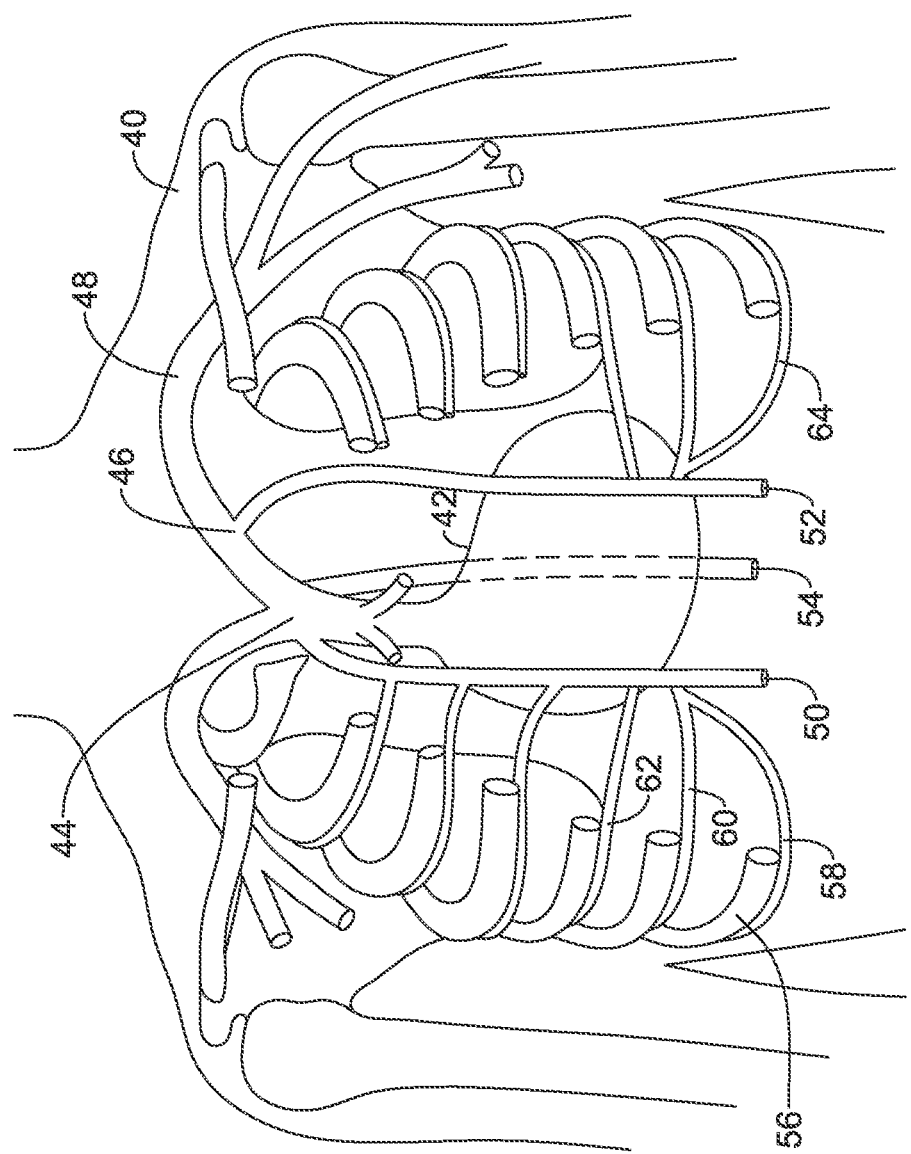
FIG. 2 shows portions of the human torso anatomy including certain venous structures.

FIG. 2 shows portions of the human torso anatomy including certain venous structures. In FIG. 2 a human torso 40 is shown with portions of the ribs and sternum omitted in order to allow the heart 42 to be observed relative to several blood vessels. The superior vena cava is shown at 44 with the brachiocephalic vein 46 feeding therein. More superior and lateral one observes the subclavian vein 48, which is commonly used for implantation of transvenous leads with intracardiac electrodes used in transvenous pacemakers and defibrillators. The azygos vein is shown at 54 and attaching to the posterior of the superior vena cava 46, running posterior to the heart (as indicated by the phantom lines); the azygos vein 46 has occasionally been noted as a potential implant location for a lead or electrode for various cardiac and/or neurological purposes.

The internal thoracic vein (ITV) is a vessel that drains the chest wall and breasts. There are both left and right internal thoracic veins on either side of the sternum, beneath the ribs. The ITV arises from the superior epigastric vein and musculophrenic vein, accompanies the internal thoracic artery along its course and terminates in the brachiocephalic vein. In FIG. 2, the right ITV is shown at 50, and the left ITV is shown at 52. The ITV has sometimes also been referred to as the internal mammary vein, though such usage has become less common in the literature. The ITV may be used as an implantation location for a pacemaker or defibrillator lead, as disclosed in are discussed in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

Implantation may be achieved by accessing the superior epigastric vein inferior to the lower rib margin and advancing a lead superiorly into the ITV 50/52. Implantation may be achieved as well by accessing the musculophrenic vein that runs along the lower rib margin, and advancing a lead superiorly into the ITV 50/52. Implantation may also be achieved by parasternal access through an intercostal space and into the ITV 50/52. Parasternal access and access via the superior epigastric or musculophrenic veins may be achieved by first finding and entering the relevant vessel with a cut-down or Seldinger technique (or other vascular access method), using, for example, an ultrasonic needle to find the correct blood vessel within the patient tissue.

In some examples, implantation may be achieved using a superior access with entry using, for example, the subclavian vein 48, advancing to the brachiocephalic vein and then through the ostium and into the ITV 50/52. Again, any suitable vascular access method including a cut-down or Seldinger technique may be used.

The ITV also receives blood flowing from the intercostal veins. The intercostal veins run adjacent and inferior to the ribs, such as with intercostal vein 58 that is shown alongside the 7$^{th}$ rib 56. Additional right side intercostal veins are shown at 60 and 62, and left side intercostal veins are also shown including at 64. The intercostal veins may also be used for implantation of a pacemaker or defibrillator lead, as discussed in U.S. Provisional Patent Application Ser. No. 62/437,063, titled IMPLANTATION OF AN ACTIVE MEDICAL DEVICE USING THE INTERCOSTAL VEIN, the disclosure of which is incorporated herein by reference. The present inventors have determined that, in addition to, or as an alternative to, inserting, in one or both ITV, a therapy lead having defibrillation, pacing, and/or sensing electrodes thereon, a lead may include a transducer to provide energy to an intracardiac pacing device such as a leadless cardiac pacemaker. In some still further examples, the ITV may not be used and instead a lead may be placed in the intercostal vein directly and to have the ultrasound transducer reside therein or, alternatively, the lead may be advanced posteriorly to the hemiazygos, accessory hemiazygos, or azygos vein, with a transducer or one or more electrodes in any of these veins.

Figure 3:
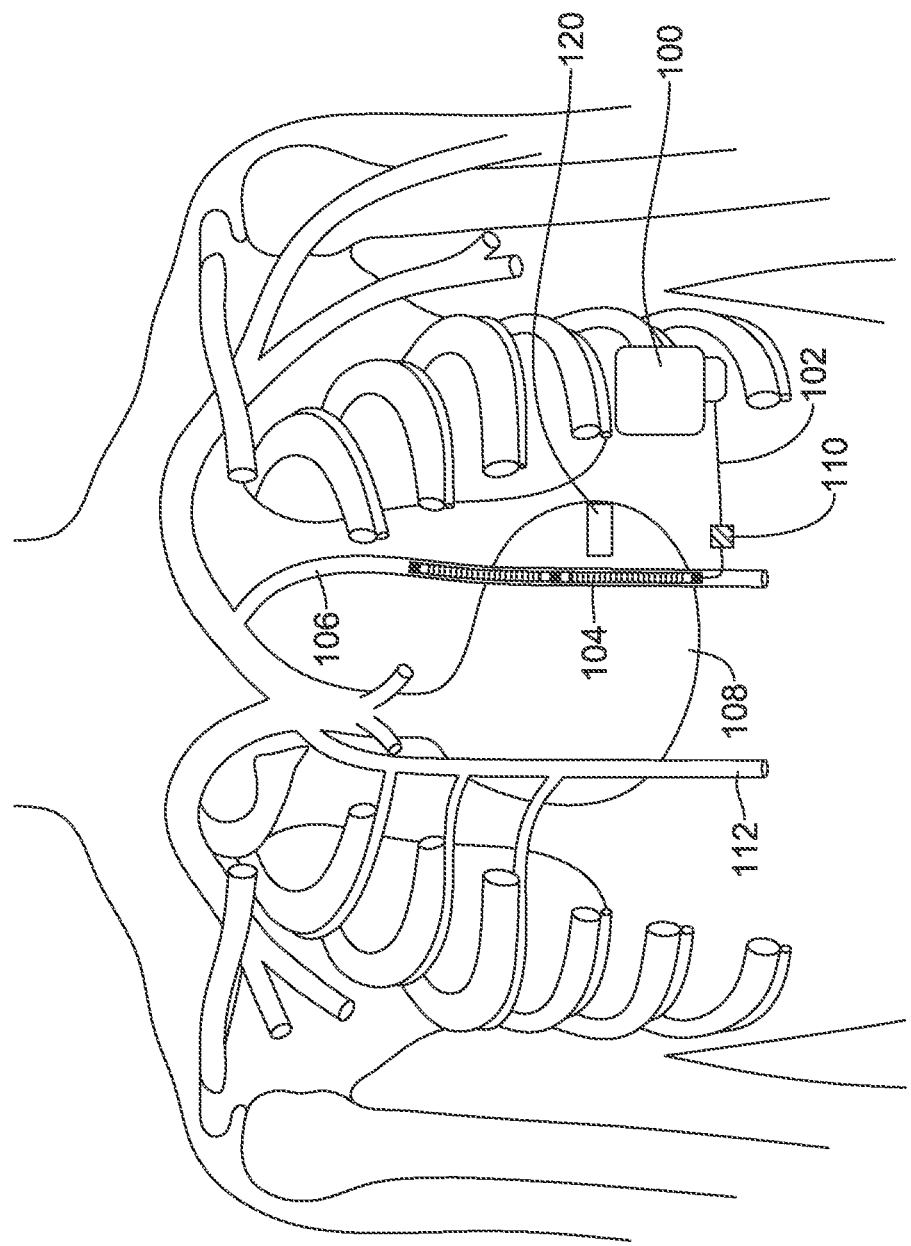
FIGS. 3-4 show implantation of illustrative cardiac therapy systems.
Figure 4:
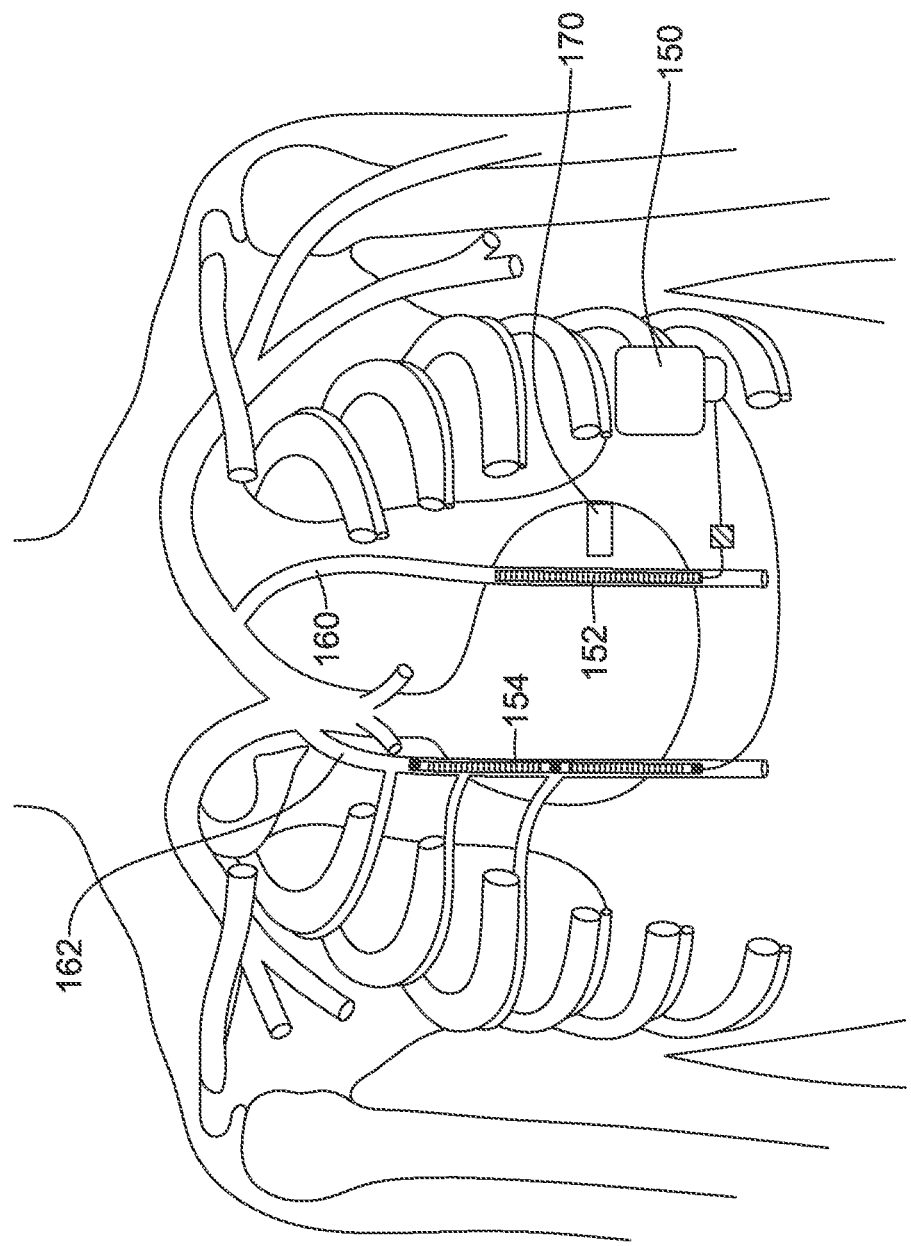

FIGS. 3-4 show implantation of illustrative cardiac therapy systems. Referring to FIG. 3, a system comprising a canister 100 is shown implanted with a lead 102 having a transducer 104 placed in the left ITV 106 of a patient. The implantation shown has the canister 100 approximately at the anterior axillary line (mid-axillary or posterior axillary lines may be used instead, or other implant location). The lead 102 may be placed in one of several ways. In one example, the lead 102 may be placed by using a parasternal access to the ITV in an intercostal space; in another example, the lead 102 may be placed by first entering the superior epigastric vein or musculophrenic vein and then advancing superiorly into the left ITV 106. In another example, access to an intercostal vein is made at the pocket where the canister 100 is located, and the lead 102 is advanced through the intercostal vein and into the ITV; once in the ITV the lead 102 can then be advanced superiorly.

In some examples, the transducer 104 may be the only element on lead 102. In other example, the lead 102 may include one or more pacing or sensing electrodes (and associated conductors) and/or one or more defibrillation coil electrodes. In still other examples, the transducer 104 may combine both a transducer element with an electrode element such as one or more pacing/sensing electrodes and/or a defibrillation coil electrode.

The transducer 104 can be powered by driver circuitry in the canister 100 to transmit a signal to a leadless pacemaker 120 which is shown, illustratively, in the left ventricle. The driver circuitry may, for example, provide an output signal at a desired ultrasound frequency, and the transducer converts the electrical signal to a mechanical signal such as by a piezoelectric element that vibrates in response to an applied signal. The leadless pacemaker 120 may be placed as shown, anchored to the myocardium inside the left ventricle using, for example, tines or a helical screw, or other fixation.

The leadless pacemaker 120 may instead by placed on the outside of the heart 108 on the left ventricle or in the coronary vasculature such as in a coronary vein on a desired part of the heart. The leadless pacemaker 120 may be placed in the right ventricle attached to the septum or in the myocardium such as in an apical position. The leadless pacemaker may instead be pleased in an atrial position such as in the right atrium, attached to the septum. Various possible implant locations are shown below in FIG. 15. The transducer 104 may be placed in the left ITV 106 or right ITV 112, and the location for the transducer 104 may be selected to bring it into proximity to the leadless pacemaker 120. Thus, in the example shown, the transducer 104 is in the left ITV which may be generally over the interventricular sulcus, the groove separating the left and right ventricle; depending on patient anatomy the left ITV may instead be more or less over the left ventricle. During placement, visualization may be used, such as fluoroscopy, to allow placement at a position more or less level with the leadless pacemaker 120. In another example, the transducer 104 may be placed in an intercostal vein such as on the left side of the patient to place the transducer more laterally to a position over the left ventricle itself. FIG. 16, below, shows various options for placing the transducer in proximity to the leadless pacemaker.

FIG. 4 shows another example. Here, the canister 150 is again in a left axillary position, and now a bifurcated lead (which may instead be two separate leads in another example) is placed, with a transducer 152 placed in the left ITV 160 and a therapy electrode 154 in the right ITV 162. For example, the therapy electrode 154 may include one or more coil electrodes for delivering higher energy therapy such as cardioversion or defibrillation, and/or may include one or more pacing or sense electrodes such as one or more ring electrodes. Again, the transducer 152 is shown in proximity to a leadless pacemaker 170.

An ultrasound transducer on a lead as shown in FIGS. 3-4 may use a piezoelectric element coupled to a sources of electricity by one or more conductors extending through the lead, such as disclosed in U.S. Pat. No. 6,654,638, the disclosure of which is incorporated herein by reference. In another example, the transmitter may take the form of a thin film ultrasound transducer (see, e.g., U.S. Pat. No. 9,440, 258, for example). When energy is transmitted by the transmission circuitry of the implantable pulse generator, the transmission element generates a mechanical signal, preferably an ultrasound signal, which is delivered across the tissue to the seed pacemaker.

Delivery, tissue attachment and retrieval features may be included in the leadless pacemaker including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Delivery, fixation and retrieval structures may also resemble that of the Micra™ (Medtronic) or Nanostim™ (St. Jude Medical) leadless pacemakers, or the WiSE CRT (EBR Systems, Sunnyvale, Calif.).

FIGS. 5-8 show distal ends for a number of illustrative leads. As noted above, in several embodiments a lead may include a transducer standing alone, a transducer and one or more of pacing, sensing and/or defibrillation electrodes, and may include a combination transducer/electrode design such as a combined defibrillation electrode and transducer. The transducers may be designed to have an ultrasound driver in the canister of the associated powering device or may instead have a miniaturized ultrasound driver integrated into the lead.

FIG. 5 shows an example lead 200, the distal end of which is shown in an ITV 202. The design may include a proximal sensing electrode, a transducer 206, and a distal sensing electrode 208. In this example the lead 200 has a design which adopts a curvature to fix it in place within the ITV 202 by pressing against opposing walls thereof along its length. For implantation, the lead 200 may be held in a straight configuration by inserting a straightening wire, such as a stylet or guidewire, therein. Alternatively, the lead may include one or more tines, expandable elements (such as a stent-like design or inflatable member) or other fixation apparatuses. Various fixation mechanisms and designs are shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

In some examples, rather than residing in the ITV 202, the lead may exit the ITV and enter into the mediastinum. Such an approach is described, for example, in U.S. patent application Ser. No. 15/814,990, titled TRANSVENOUS MEDIASTINUM ACCESS FOR THE PLACEMENT OF CARDIAC PACING AND DEFIBRILLATION ELECTRODES, and Ser. No. 15/815,051, titled ELECTRODE FOR SENSING, PACING, AND DEFIBRILLATION DEPLOYABLE IN THE MEDIASTINAL SPACE, the disclosures of which are incorporated herein by reference.

In several examples herein, the lead may be placed without entering, or contacting the heart. The transducer is placed, in several examples, at a location which is beneath the ribs, or in plane with the ribs, without entering or contacting the heart.

FIG. 6 shows another example. Here the lead 220 includes a distal defibrillation coil electrode 222 and a proximal defibrillation coil electrode 224, with a transducer 226 therebetween. A distal tip pace/sense electrode is shown at 230 and a proximal pace/sense electrode is shown at 232. Fixation designs and elements as described above may also be included.

FIG. 7 shows another example. Here, the lead 240 includes a combination defibrillation electrode and transducer 242, with a plurality of sensing/pacing electrodes at 244, 246, 248. As shown below in FIGS. 9-10, the combination electrode/transducer may include a transducer within a coil, or the transducer may be contained in a lumen within the lead.

FIG. 8 shows another example. Here, the lead 260 comprises first and second transducers 262, 264 and a plurality of sense/pace electrodes 266, 268, 270. The transducers 262, 264 may be separately addressable by the device, or may operate in unison. In one example, each transducer 262, 264 may be operable relative to a common ground wire within the lead, with each having a separate "hot" wire going thereto.

Figure 9:
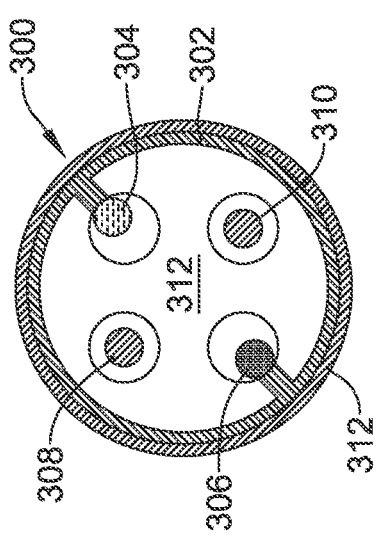
FIGS. 9-10 show illustrative leads in cross section.
Figure 10:
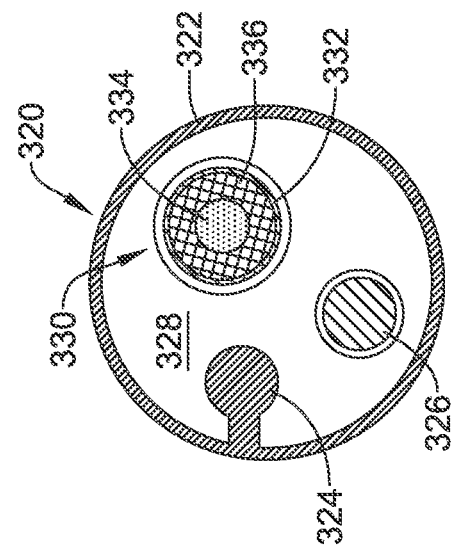

FIGS. 9-10 show illustrative leads in cross section. In FIG. 9, a lead 300 is shown in a section view with a sheet-type piezoelectric transducer 302 on the outside of the lead, with a defibrillation coil 312 placed thereover. The piezoelectric transducer 302 is driven by a pair of conductors 304, 306 acting as anode and cathode, delivering a driver signal to the transducer 302 from a driving circuit in an associated canister (FIG. 3, item 100, for example). Additional conductors 308, 310 may be provided to couple to the coil electrode 312 in lumens defined in the lead insulator 312.

FIG. 10 shows another example. Here, the lead 320 is again shown in cross section, with a defibrillation coil 322 on the outside of the lead body 328, coupled to a conductor 324 by weld, adhesive, and/or staking, for example. A lumen 330 is provided and contains an ultrasound transducer 332 on a carrier having one or more conductors 334 in a transducer body 336.

In other examples, the outer coil 312 (FIG. 9) or coil 322 (FIG. 10) may be omitted such that the transducer is the sole active element at a given axial location on the lead. Any suitable electrode, conductor, and lead body material may be used, as desired.

Figure 11:
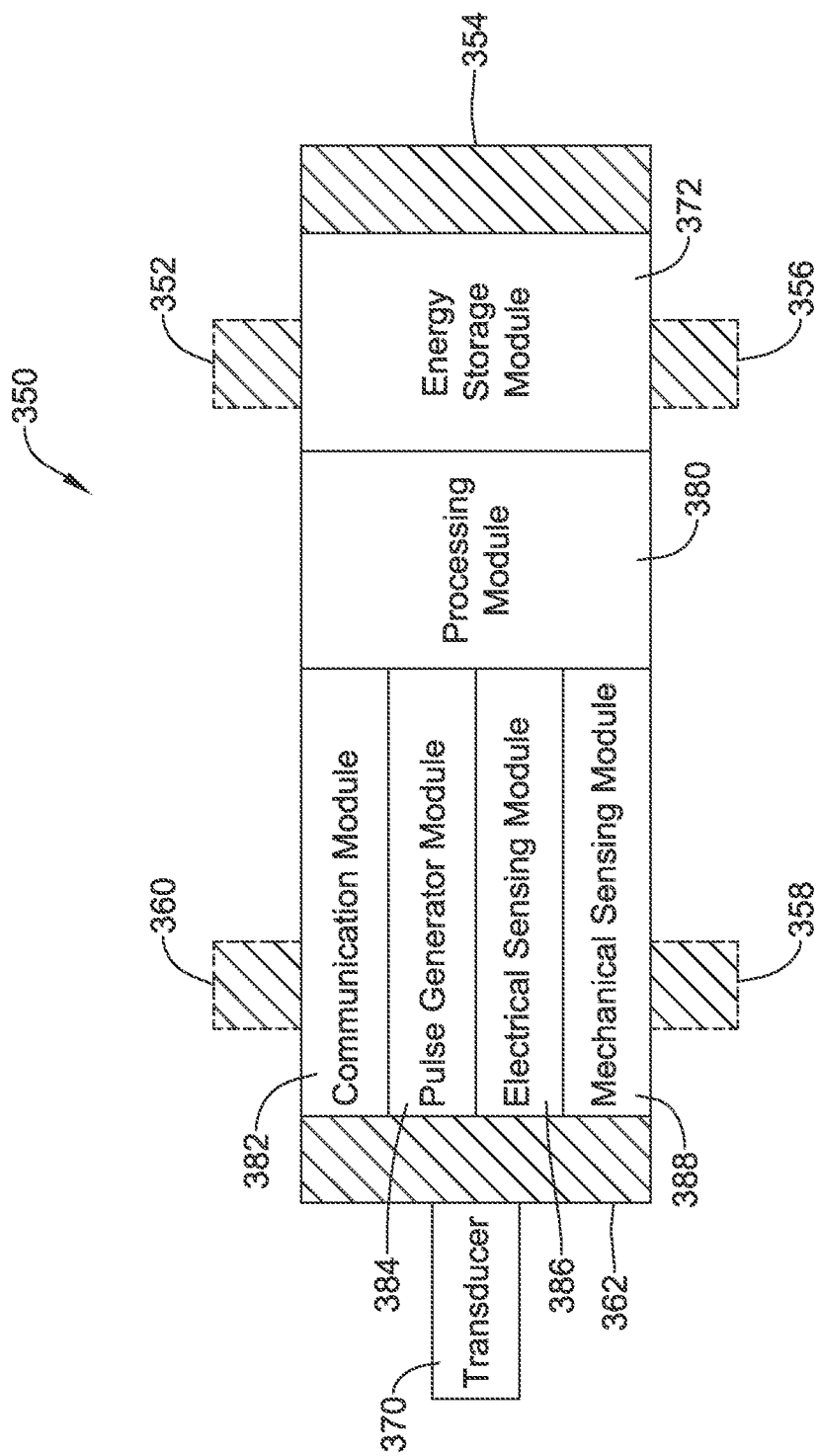
FIGS. 11-13 show illustrative implantable devices adapted to receive power from another implantable device.
Figure 12:
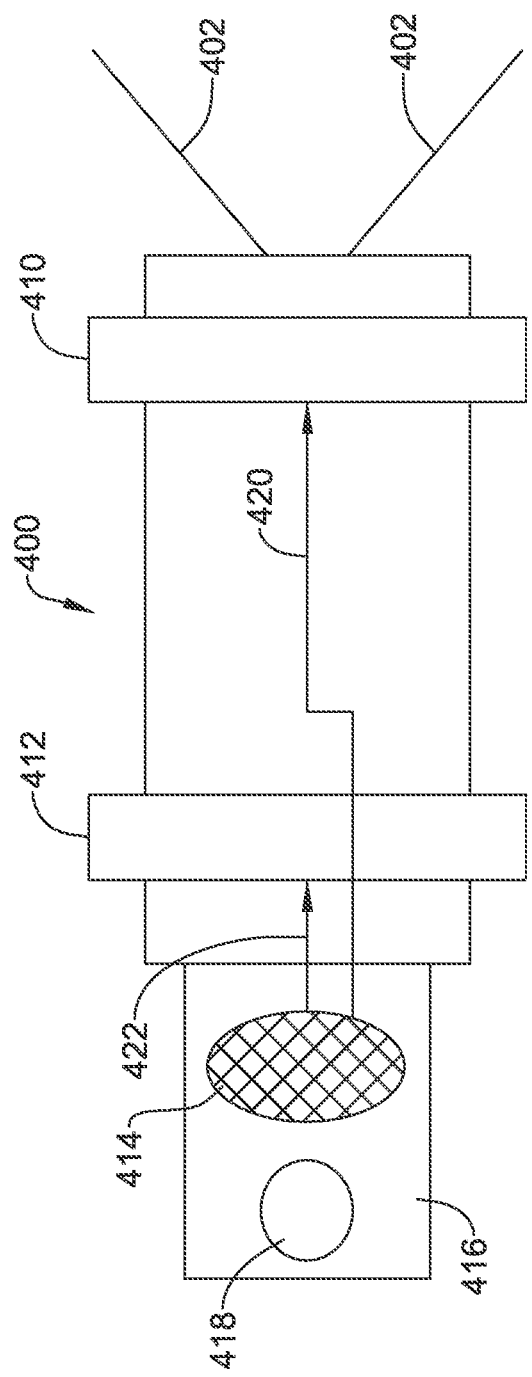
Figure 13:
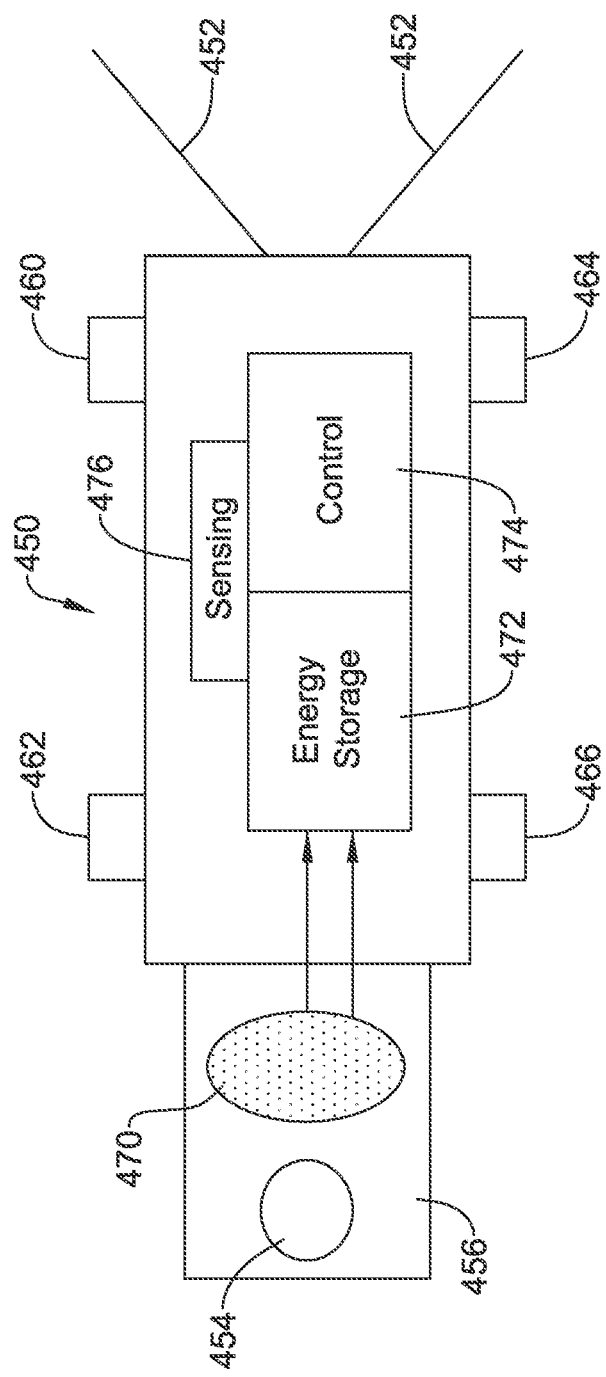

FIGS. 11-13 show illustrative implantable devices adapted to receive power from another implantable device. Referring first to FIG. 11, a relatively full function LCP is shown at 350. The LCP 350 is shown as including several electrodes at 352, 354, 356, 358, 360, 362 which may be used for therapy delivery, signal sensing, and/or to support conducted communication.

A transducer is shown at 370. The transducer may include a piezoelectric member to convert mechanical energy, and more particularly an ultrasound signal, to electrical energy. Various references have shown the receipt of acoustic power such as an ultrasound signal for use in generating a therapy output. For example, U.S. Pat. Nos. 3,659,615; 3,735,756; 5,193,539; 6,140,740; 6,504,286; 6,654,638; 6,628,989; 6,764,446; 7,890,173; 9,180,285; 9,343,654; and 9,452,286, for example, as well as U.S. Patent Application Publications 2002/0077673; 2004/0172083; and 2004/0204744, the disclosures of which are incorporated herein by reference. The transducer 370 converts the received mechanical signal into an electrical signal which can then be rectified and smoothed and/or stored on a capacitor or rechargeable battery as part of an energy storage module 372. The energy storage module 372 may further include a non-rechargeable or "primary" battery cell.

Though not shown, a retrieval feature may be included, for example, as an opening on or near the transducer to allow a retrieval tool to attach thereto. A number of tines (not shown) may extend from the device in several directions. The tines may be used to secure the device in place within a heart chamber. An attachment structure may instead take the form of a helical screw, if desired. In some examples, tines are used as the only attachment features. As noted above, delivery, tissue attachment and retrieval features may be included in the LCP including those features shown in US PG Patent Publications 20150051610, and/or 20150025612, titled SYSTEM AND METHODS FOR CHRONIC FIXATION OF MEDICAL DEVICES, for example. Delivery, fixation and retrieval structures may also resemble that of the Micra™ (Medtronic) or Nanostim™ (St. Jude Medical) leadless pacemakers, or the WiSE CRT (EBR Systems, Sunnyvale, Calif.). Some fixation examples are also shown below.

The device 350 is shown with several functional blocks including a processing module 372 which may include, for example, one or more microprocessors and associated memory, input/output and/or logic circuitry, or any other suitable circuitry, to allow instructions to be stored and executed as needed. The processing module 380 may additionally or instead include a state machine architecture.

The device is also shown with a communications module 382, a pulse generator module 384, an electrical sensing module 386, and a mechanical sensing module 388. In some examples, the electrical sensing module 386 and mechanical sensing module 388 may be configured to sense one or more biological signals for use in one or more of determining timing for cardiac resynchronization therapy (CRT), identifying physiological conditions, such as those affecting the parasympathetic nervous system that may affect CRT timing needs, and/or for assessing CRT efficacy, as further described below. The mechanical sensing module 388 may alternatively include a motion sensor to detect whether the patient is active or not in order to support a rate adaptive pacing protocol that increases the pacing rate when the patient is active. In still other examples, the mechanical sensing module may include a temperature sensor, a chemical sensor, a heart sound sensor, or any other sensor, to provide information to support any of pacing, rate adaptive pacing, CRT, or to provide diagnostics to aid in patient condition determinations.

The processing module 380 may receive data from and generate commands for the other modules 382, 384, 386, 388. Processing module 380 may also obtain information from and/or control operations in the transducer and/or energy storage module. For example, if a rechargeable battery is being used, the processing module (or the energy storage module 372) may determine when to turn on or off the pulse generator module if the rechargeable battery is running low. In another example, the processing module may determine that the energy storage module 372 is running low and then use the communications module 382 to request recharging from a separate implantable device. In addition, the processing module 380 and/or energy storage module and/or transducer may include over-charge and/or over-voltage protection circuitry, zero volt recharge circuitry (to prevent damage to the energy storage module on recovery from a complete discharge of the energy storage module 372) and any other suitable features to enhance reliability and/or protect patient safety in relation to the use of a transducer and energy storage module 372.

Various details and/or examples of internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the WiSE CRT (EBR Systems, Sunnyvale, Calif.); Micra™ (Medtronic) or Nanostim™ (St. Jude Medical) leadless pacemakers. Circuity useful in relation to the recharging circuitry, communication circuitry, and/or pulse generator circuitry, may also be found in U.S. Pat. Nos. 7,177,698, and 7,437,193, the disclosures of which are incorporated herein by reference.

FIGS. 12-13 show leadless pacemakers with reduced functionality. In FIG. 12, a device 400 includes tines 402, 404 for fixation on one end thereof. Electrodes are shown as ring electrodes at 410, 412 for therapy delivery. A removal feature 418 is shown as a grasping hole for receiving a retrieval tool on a tab 416 extending out from the body of the device.

A transducer is shown at 414 for receiving mechanical energy and converting the mechanical energy into electrical energy. The outputs of the transducer 414 may feed more or less directly to the electrodes 410, 412 for therapy output, making this device purely a receive—and—deliver system. Regulating and/or control circuitry may be included to, for example, prevent therapy delivery below a received energy threshold and/or cap the therapy output within a safety margin.

A direct feed of the signal may be deliver a sinusoidal output therapy signal. If desired, additional rectification and control circuitry may be provided to further shape the therapy output, if desired, to yield, for example, a square wave in a monophasic or biphasic form. For example, the transducer signal 414 may go through a rectifier to a smoothing capacitor to generate more or less constant, monophasic signal. A switch relying on timing circuitry (such as a timing capacitor) may be provided to reverse polarity at some predefined interval. In order to allow a single device to be addressed, the transducer and associated circuitry may be tuned to a particular frequency, allowing only ultrasound frequency within a predefined bandwidth to generate a response, avoiding the potential for interference form known sources such as therapeutic or imaging ultrasound, if desired, or allowing a single leadless device among several implanted devices to be addressed by selecting an appropriate frequency band.

FIG. 13 illustrates a hybrid device. The device 450 again includes tines 452 for fixation and a removal feature shown at 454 on tab 456. Other fixation designs may be used instead. A number of electrodes are provided, this time as posts rather than rings, and shown at 460, 462, 464, 466. A transducer 470 for receiving mechanical energy and converting to electrical energy delivers current/voltage to an energy storage block at 472. A control circuit is shown at 474, and a sensing circuit is shown at 476. This system may use the control circuitry to control therapy output using the electrodes 460, 462, 464, 466, with power from the energy storage block 472.

The concept may be to provide a short term "rechargeable" device, with an expected rechargeable life of, for example, seven days or less, for example, a device capable of going one to three days between charging may be used. In such a case, recharging may occur while the patient is at rest (at night, for example), when the delivered power will not encounter outside interference and/or the patient is not moving, preferably making energy delivery more efficient. The patient's rest may be identified by using a motion sensor in the charging device (patient still and laying down), by reference to a system clock (night time), or by observation of cardiac rate trends over a period of time (slowing and steady). Other charge periods may be used instead.

The sensing circuit 476 may offer capabilities such as including an activity sensor or any of the functions noted above with respect to the mechanical sensing block in FIG. 11, and/or may offer sensing capabilities relative to electrical signals such as the ECG. In one example, the sensing circuit is used for sensing electrical signals received at the electrodes 460, 462, 464, 466 in order to observe for conducted communication. For example, a separate device may issue ultrasound energy to trigger (or power) the device 450 to enter a listening phase with the sensing circuit, and then a 1-way or 2-way communication session may take place by conducted communication.

Data exchanged by conducted communication may include, for example, request or commands for therapy delivery, adjustments to delivered therapy, information related to patient condition (such as patient activity level), or any other suitable input. For example, a second device may use conducted communication to coordinate a pace capture testing sequence, or a second device may use conducted communication to command or adjust resynchronization therapy delivery. Some illustrative interactions are discussed in U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, Ser. No. 15/684,264, titled CARDIAC RESYNCHRONIZATION USING FUSION PROMOTION FOR TIMING MANAGEMENT, Ser. No. 15/684,366, titled INTEGRATED MULTI-DEVICE CARDIAC RESYNCHRONIZATION THERAPY USING P-WAVE TO PACE TIMING, Ser. No. 15/710,118, titled MULTI-DEVICE CARDIAC RESYNCHRONIZATION THERAPY WITH MODE SWITCHING TIMING REFERENCE, and Ser. No. 15/793,475, titled MULTI-DEVICE CARDIAC RESYNCHRONIZATION THERAPY WITH TIMING ENHANCEMENTS, the disclosures of which are incorporated herein by reference.

Return communication may be issued by the device 450, for example, to indicate completion of a charging session, to annunciate device history or error issues, or for any other suitable purpose. The implantable device 450 may be configured to deliver an output signal, therapeutic or otherwise (such as one or more signal outputs of very short duration, shorter than chronaxie, for example) for receipt by the charging device upon completion of charging.

The control circuit 474, which may be a state machine, an application specific integrated chip, or even a controller, but is more likely a set of logic configured for certain relatively limited function and power consumption, then controls delivery of pacing therapy using, for example, the sensing circuit 476 to determine whether rate adaptive pacing is needed and/or to assist in evaluating pace capture, efficacy, or any other suitable diagnostic. At intervals, such as at daily intervals or when the patient is determined to be resting, the charging of the implanted device using the transducer 470 may be initiated.

Figure 14:
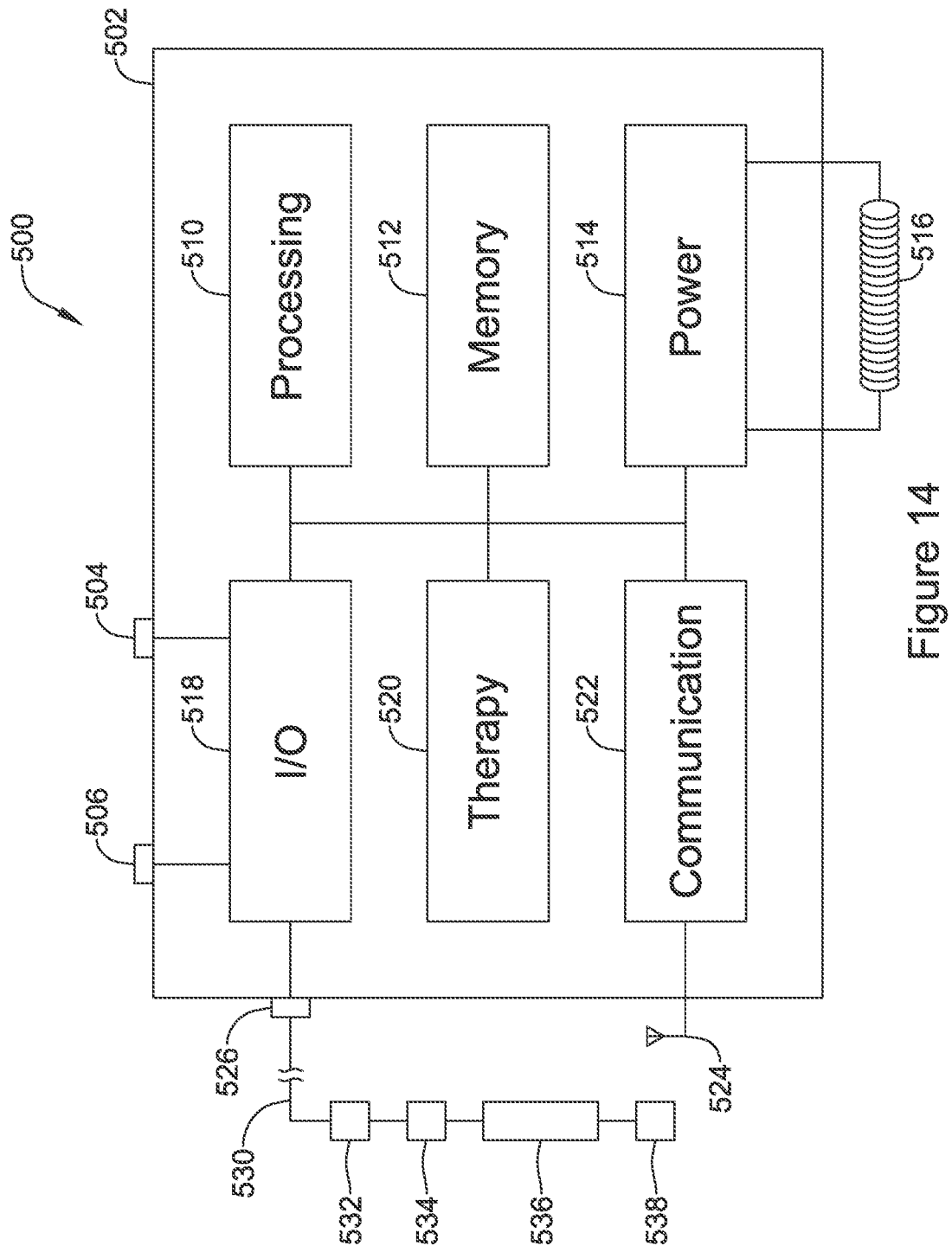
FIG. 14 shows an illustrative implantable device adapted to provide power to another implantable device.

FIG. 14 shows an illustrative implantable device adapted to provide power to another implantable device. The illustration indicates various functional blocks within a device 500, including a processing block 510, memory 512, power supply 514, input/output circuitry 518, therapy circuitry 520, and communication circuitry 522. These functional blocks make up at least some of the operational circuitry of the device. The I/O circuitry 518 can be coupled to one or more electrodes 504, 506 on the housing 502 of the device 500, and may also couple via a header 526 for attachment to one or more leads 530 having additional electrodes 532, 536, 538 and at least one transducer 534.

The processing block 510 will generally control operations in the device 500 and may include a microprocessor or microcontroller and/or other circuitry and logic suitable to its purpose. A state machine may be included. Processing block 510 may include dedicated circuits or logic for device functions such as converting analog signals to digital data, processing digital signals, detecting events in a biological signal, etc. The memory block 512 may include RAM, ROM, flash and/or other memory circuits for storing device parameters, programming code, and data related to the use, status, and history of the device 500 and/or a paired second device such as a leadless pacemaker as shown above in FIGS. 11-13 and elsewhere.

The processing block 510 may be coupled to an activity sensor to detect patient movement, posture, activity, etc. Such an activity sensor may be provided in the device 500, or may be on an associated device such as a leadless pacemaker as shown above, with patient movement, posture or activity data communicated to the processing block using conducted or other communication. The processing block 510 may be configured to sense cardiac activity, such as to identify a cardiac state of the patient (normal sinus, sinus tachycardia, ventricular or atrial arrhythmia, etc.), and/or to determine a need for therapy such as by identifying asystole or a long pause or a ventricular arrhythmia such as ventricular fibrillation. The processing block 510 may be configured to observe cardiac activity using electrical inputs (captured using electrodes 532, 536, 528 and/or 504 and 506) or using other devices such as a heart sound sensor, an accelerometer to detect cardiac motion, an optical input to detect blood flow, etc. Such observed cardiac activity may be used, as noted already, for arrhythmia identification, but it may also be used to tailor and/or optimize therapy such as by observing whether pacing therapy delivery from a leadless pacemaker is capturing the heart or otherwise having an intended effect such as improving cardiac output and/or synchronization.

Some examples of the use of a device such as device 500 to assist in therapy management of a leadless pacemaker are discussed, for example, in U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, Ser. No. 15/684,264, titled CARDIAC RESYNCHRONIZATION USING FUSION PROMOTION FOR TIMING MANAGEMENT, Ser. No. 15/684,366, titled INTEGRATED MULTI-DEVICE CARDIAC RESYNCHRONIZATION THERAPY USING P-WAVE TO PACE TIMING, Ser. No. 15/710,118, titled MULTI-DEVICE CARDIAC RESYNCHRONIZATION THERAPY WITH MODE SWITCHING TIMING REFERENCE, and Ser. No. 15/793,475, titled MULTI-DEVICE CARDIAC RESYNCHRONIZATION THERAPY WITH TIMING ENHANCEMENTS, the disclosures of which are incorporated herein by reference.

For example, modifications to leadless pacemaker operation may include suggesting or commanding changes in therapy timing, therapy type, and/or therapy amplitude or other parameters, for example the processes described in the above referenced U.S. patent application Ser. Nos. 15/633,517, 15/684,264, 15/684,366, 15/710,118, and 15/793,475. Data of this sort may be encoded in the ultrasound energy output of a transducer by, for example, varying a frequency or duration of output energy or duty cycle, or including spikes or gaps in the output to cause perturbations that may be detected by the leadless pacemaker. In other examples, data to modify leadless pacemaker operation may be communicated using conducted or other communications such as RF communication.

For example, the I/O circuitry 518 may filter and amplify cardiac signals to be provided to the processing circuitry 510 which uses instructions and parameters provided in memory to determine one or more of the following:
  Whether therapy has been delivered by the leadless pacemaker at a desired time relative to an R-wave, a P-wave, or a prior therapy output
  Whether therapy delivered by the leadless pacemaker has evoked a desired response from the heart, such as triggering a ventricular contraction, or triggering a fusion beat for cardiac resynchronization therapy
The device 500 may include, in an example, rather than an electrode at 506, an acoustic sensor or accelerometer to capture heart sounds or motion (the sensor may instead be on the lead 530) indicating whether the cardiac function is responding to pacing therapy from the leadless pacemaker to cause ventricular contraction or cardiac resynchronization. The device 500 may include, in an example, an optical sensor rather than an electrode at 506 to observe blood flow, or a sensor may be placed on the lead 530, to determine pulsatile blood flow or blood flow velocity to observe cardiac function in response to a pacing therapy delivery.

The power supply 514 typically includes one to several batteries, which may or may not be rechargeable depending on the device 500. For rechargeable systems there would additionally be charging circuitry for the battery including for example a coil 516 for receiving energy and regulating and rectification circuitry to provide received energy to a rechargeable battery or supercapacitor.

The I/O circuitry 518 may include various switches or multiplexors for selecting inputs and outputs for use. I/O circuitry 518 may also include filtering circuitry and amplifiers for pre-processing input signals. In some applications the I/O circuitry will include an H-Bridge to facilitate high power outputs, though other circuit designs may also be used. Therapy block 520 may include capacitors and charging circuits, modulators, and frequency generators for providing electrical outputs. The therapy block and/or I/O block 518 includes driver circuitry for driving the transducer 534 with an ultrasound-frequency range signal. For example, the driving frequency may be in the range of about 20 kHz to about 10 MHz. The driver and transducer 534 may be designed to have a controllable frequency to allow separate addressing of multiple implanted devices that are appropriately tuned.

In some examples, the I/O circuitry 518 and therapy block 520 may be designed such that one or a pair of contacts in the header 526 are dedicated for use as mechanical transducer drivers. In other examples, the driver circuitry for mechanical transducer may be multiplexed with other I/O circuits. Thus, for example, any contact, or several contacts, in the header 526 may be configurable for use as sense-receive signal contacts, pace or defibrillation electrical therapy outputs, and/or coupling to a mechanical transducer 534 in the lead 530.

In one example, the driver circuitry provides a single output which is routed to different output contacts in the header 526 to drive separate transducers in the lead 530 or a plurality of leads, with different transducers being addressed at different times using a switch network of the I/O circuit. For this example, the driver circuit may generate outputs at different frequencies at different times to use a given transducer for a selected purpose. Thus, for example, a system may have a first transducer located on a first lead in the right ITV for delivering energy to a first leadless pacemaker in the right ventricle (the "RV device"), and a second transducer located on a second lead in the left ITV for delivering energy to a second leadless pacemaker located in a coronary vein on the left side of the heart (the "LV device"). To achieve selectivity, the driver circuit may generate a first output tuned for the RV device using a first frequency at a first time and using a first combination of contacts in the header as selected using the I/O circuitry thus coupling the signal to the first transducer, and also generates a second output tuned for the LV device using a second frequency at a second time that does not overlap the first time and using a second combination of contacts in the header as selected using the I/O circuitry thus coupling the signal to the second transducer. In other examples, the driver circuit may have multiple outputs and/or may be capable of generating multiple outputs at a given time.

In still other examples, all the leadless pacemakers in a given system may use the same, or at least similar, frequencies to receive mechanical energy, and the frequency selectivity may be unnecessary; to optimize the output power usage, multiple transducers may be powered at the same time at one frequency; if desired, one transducer may be phase shifted to avoid destructive interference of the signals and/or to prevent delivering too much power at a given location due to constructive interference. Such phase shifting may occur by placing a variable filter element in line with one of the output circuits. If interference is a concern, another solution may be to power only one transducer at a time.

The communication circuitry 522 may be coupled to an antenna 524 for radio communication (such as Medradio, ISM, Bluetooth, or other radiofrequency protocol/band), or alternatively to a coil for inductive communication, and/or may couple via the I/O circuitry 518 to a combination of electrodes 504, 506, 532, 534, 538, for conducted communication. Communication circuitry 522 may include a frequency generator/oscillator and mixer for creating output signals to transmit via the antenna 524. Some devices 500 may include a separate or even off-the shelf ASIC for the communications circuitry 522, for example. For devices using inductive communication an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 14. For example, some devices may include a Reed switch, Hall Effect device, or other magnetically reactive element to facilitate magnet wakeup, reset, or therapy inhibition of the device by a user, or to enable an MM detection and/or MM protection mode(s).

A device as in FIG. 14 may be embodied as a subcutaneous implantable defibrillator with the additional capability for providing energy using transducer 534 to a second implantable device. For example, transducer 534 may be on a separate lead that is implanted in the ITV, while the device also uses a subcutaneously placed lead for sensing and defibrillation purposes.

Figure 15:
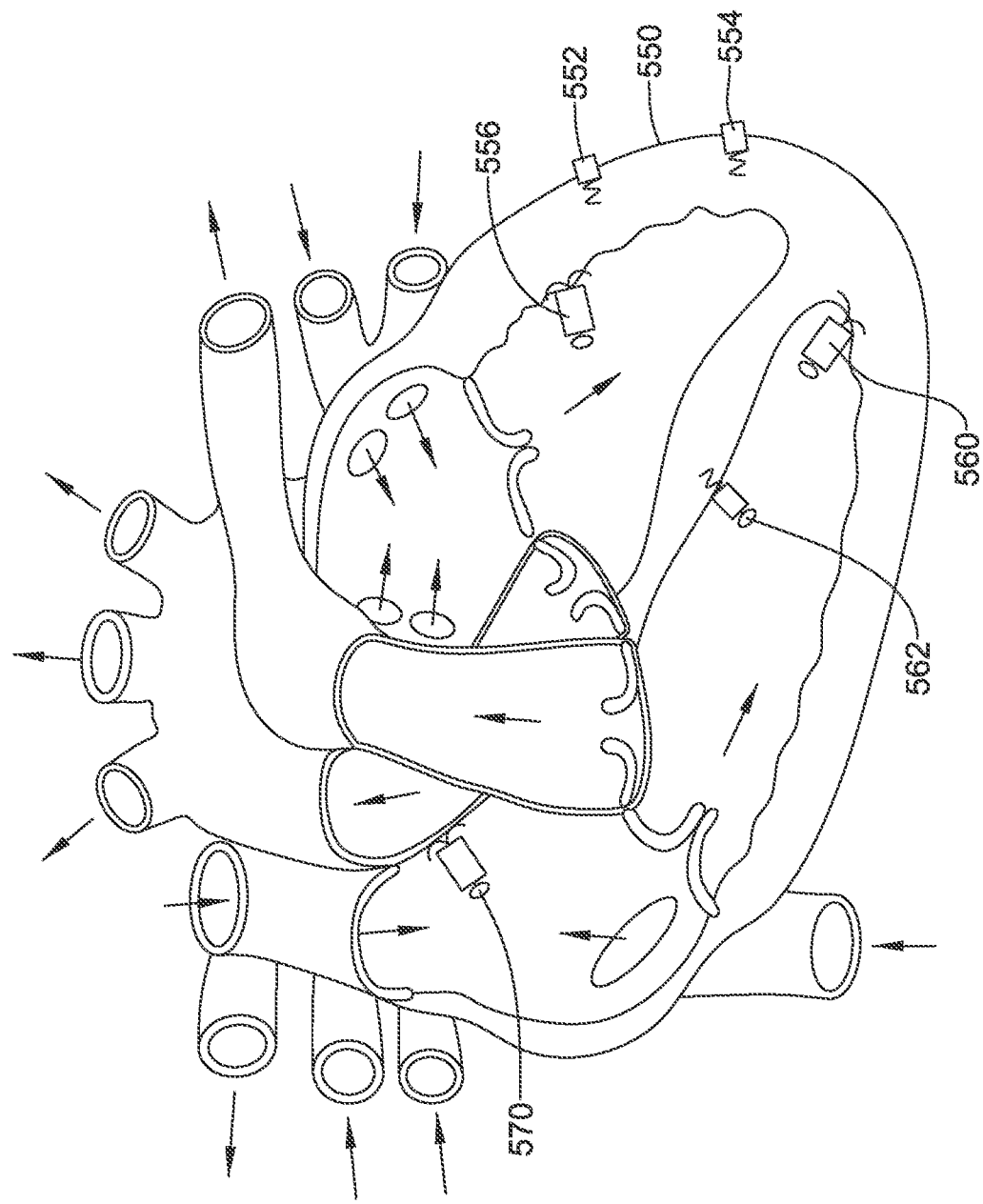
FIG. 15 shows a human heart with several potential implant locations for illustrative medical devices highlighted.
Figure 16:
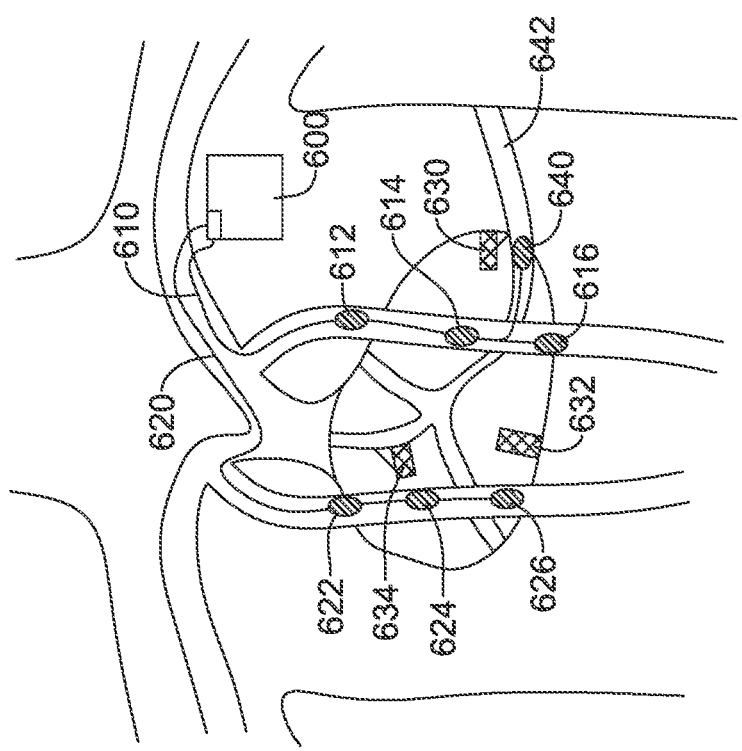
FIG. 16 shows a set of transducer locations that may be used in several embodiments.

FIG. 15 shows a human heart with several potential implant locations for illustrative medical devices highlighted. A leadless cardiac pacemaker as shown herein could be implanted at numerous locations in or on the heart 550. For example, devices may be implanted as shown at 552, 554, on the outside of the heart by the left ventricle. A device may be implanted inside the left ventricle as shown at 556. Devices may also be placed in the right ventricle, for example at the apex as shown at 560 and/or into the interventricular septum at 562. A device may be placed in the right atrium if desired, as shown at 570, anchoring to the atrial septum. An atrial position may be easier if the size and/or mass of the device are reduced by using one of the less complex designs shown above in FIGS. 12 and 13, as opposed to a more full-function device as shown by FIG. 11 (though the device of FIG. 11 may still be used). Devices may be affixed in place using tined or helical structures as desired; the actual structures shown are merely illustrative.

In some examples, multiple devices may be placed. For example, a system may be designed with devices that are provided in sets, with or without dedicated purposes (i.e. a set may include an LV device and an RV device as well as an RA device—each having a dedicated purpose—or a set may include devices A, B, C, each of which is generic as to location), where each device in a set is tuned to receive energy using a transducer at a different frequency. In another example, the control circuitry of a device may be able to set the transducer to tune to one of several predetermined frequencies either as part of a preoperative setup of the device, or by communication in-vivo. Such tuning may allow, for example:

A single extracardiac device to selectively activate a plurality of implantable devices from one or more transducers by selecting an output frequency A single extracardiac device to charge separately each of a plurality of implantable devices from one or more transducers using frequency selection Another scenario is that an extracardiac device issues both a mechanical signal (using, for example, ultrasound) as well as an electrical signal to selectively activate or command pacing with different pace modules. For example, a device as in FIG. 13 may sense for a conducted communication signal to determine when to deliver therapy, while it receives power via a transducer. This design would be different from the Prior Art of FIG. 1 insofar as in the existing commercially available (in Europe at least) system from EBR Systems, a large subcutaneous transducer is used by the powering, subcutaneous device, in order to ensure that enough power is output to trigger the leadless cardiac pacemaker immediately. Assuming, for example, that the pace therapy has a pulse width of 5 to 15 milliseconds and is delivered at a rate of 75 beats per minute, the duty cycle of the EBR Systems transducer/transmitter would be about (75*0.015/60)<2% relative to a one-minute time reference. While some examples may facilitate on-demand pacing where the transducer operation correlates to the pacing output, other examples may adopt a different approach.

More particularly, in some examples, a smaller transmitter/transducer may be used if the output power is lowered and the duty cycle is increased to, for example, at least 10% or even up to 100% relative to an extended time period such as a minute, hour, or day, or longer. A range of about 20% to about 40% may be used in some examples. At a duty cycle of, for example, 20%, referenced to a day, the charging could take place in a bit under five hours while the patient sleeps, for example, to charge for a generally continuous block of time. A duty cycle of, for example, 20% relative to an hour would allow charging to be scheduled throughout the day including, for example, charging for about twelve minutes, or more, once every hour. Still shorter time periods may be used.

While some examples will include the leadless pacemaker providing an indication that charging is complete via, for example, conducted communication, other examples may omit such a step. The leadless pacemaker may, for example, communicate with the charging device infrequently, such as daily or weekly, to configure pacing and charging parameters. The operational circuitry of the charging device will then set charging parameters to ensure that charging is performed to keep the leadless pacemaker sufficiently charged for its therapy burden. For example, the operational circuitry may determine how often the leadless pacemaker would exhaust a fully charged rechargeable battery or capacitor, and would trigger recharging at times selected to avoid exhausting the leadless pacemaker power supply; recharging cycles may thus be triggered according to expected need, rather than on a periodic (hourly or daily, for example) basis. Charging efficiency may also be determined by querying the leadless pacemaker as to the duration of time needed to charge its power supply from a known state of at least partial discharge to a fully charged state; charging efficiency may depend on patient physiology and device placement, for example. Such processes may be performed by the implanted system on its own, or may be facilitated by an external programmer if desired.

The leadless pacemaker would receive power and store electrical energy on a capacitor or rechargeable battery, for example. In such a design, the leadless pacemaker may itself control therapy delivery timing, or it may receive a signal, such as an interruption in the transmitted mechanical energy or a separately conveyed signal such as a conducted communication signal or an RF or inductive signal, to trigger pacing therapy. The triggered pacing therapy may comprise a single pacing pulse output or a sequence of pacing such as a set of anti-tachycardia pacing pulses.

A temperature sensor may be provided in proximity to the transducer on the lead to monitor for any changes in temperature that may suggest local heating at the transducer; in the event of heating the transducer may be duty cycled off to avoid tissue damage, discomfort, or malfunction. Similarly a temperature sensor may be provided in association with the driver in the implantable device housing. Cycling may be performed by, for example, turning a transducer on for a period of, for example, one to twenty seconds, and then turning the transducer off for a period of, for example, one to sixty seconds.

Still further options for implantation of a leadless pacemaker may include those shown in U.S. Pat. No. 8,103,359, the disclosure of which is incorporated herein by reference. For example, a leadless pacemaker may be provided in one of the coronary veins, with recharging using an ultrasound (or other transducer) located as shown in any of the various examples shown herein. Such a leadless pacemaker may be implanted through anchoring to the blood vessel wall, by using a bias member to create an anchoring position in the blood vessel, or by attaching a short lead to secure the device in place using a deployable coil or stent structure, as shown further in the '359 patent. The inclusion of such anchoring structures, which are generally deployed within a single blood vessel or chamber of the heart, is within the intended meaning of a "leadless pacemaker" as used herein.

FIG. 16 shows a set of transducer locations that may be used in several embodiments. This example shows a device canister at 600 implanted in a position that is commonly used for transvenous pacemakers, with two leads 610, 620 extending therefrom. A first of the leads 610 extends into the left ITV and is shown with several transducers at 612, 614 and 616 in the ITV. Optionally, one or more transducers 640 may be implanted in an intercostal vein 642. The other lead 620 extends across to the right ITV via the brachiocephalic vein, and includes several transducers at 622, 624, 626. It is unlikely that a single device 600 would be used with six or even seven transducers as shown; the Figure is provided for illustration and it should understood that one or more of the transducers shown may be omitted in an actual system. The patient is shown as having a left ventricular leadless pacemaker 630, a right ventricular leadless pacemaker 632, and an right atrial/septal leadless pacemaker 634. Such a configuration may be useful for heart failure, for example.

In another example, one or more of the illustrated leadless pacemakers may also be implanted in a coronary vein as shown by U.S. Pat. No. 8,103,359, the disclosure of which is incorporated herein by reference. For example, a coronary vein (such as in the coronary sinus) placed leadless pacemaker may be combined with a right ventricular leadless pacemaker, with the device placed in the coronary sinus providing LV pacing and/or sensing; one or both of the leadless pacemaker devices may also receive energy from a transducer located, for example, in the ITV, in an intercostal vein, or even an azygos, hemiazygos, or accessory hemiazygos location.

Depending on the specific locations of the implanted leadless device 630, 632, 634, different ones of the transducers may be selected to provide power; such selection may be based on proximity and physician preference. For example, transducers 622, 624 may be activated—individually or together—to power a nearby device in the right atrium 634. Transducer 626 may be used to power a right atrial device 632; if needed or desired (for example, if device 632 is quite medial compared to each ITV), transducer 616 may also be used to power the right atrial device 632, alone or in combination with transducer 626. Transducers 614, 616, and 640 (individually or in combination) may be used to power the left ventricular device 630. If a patient has multiple implanted devices 630, 632, 634, the different devices and associated transducers may be configured to use uniquely selected frequencies or bands of frequencies to allow the devices to be separately addressed. In some examples, on the other hand, power transmission may occur at a single frequency for all devices, with other signals provided to the individual devices for control purposes using, for example, conducted communication, or RF or inductive links.

In another example, the system may integrate multiple functions to allow cardiac rhythm management, for example, heart failure or rate adaptive pacing for a patient with a complete block. In such an example, the leads 610, 620 may also include sensing electrodes to allow sensing of atrial and/or ventricular signals for use in providing cardiac resynchronization therapy (CRT) and/or to provide ventricular pacing using atrial timing for a patient with complete heart block.

Figure 17:
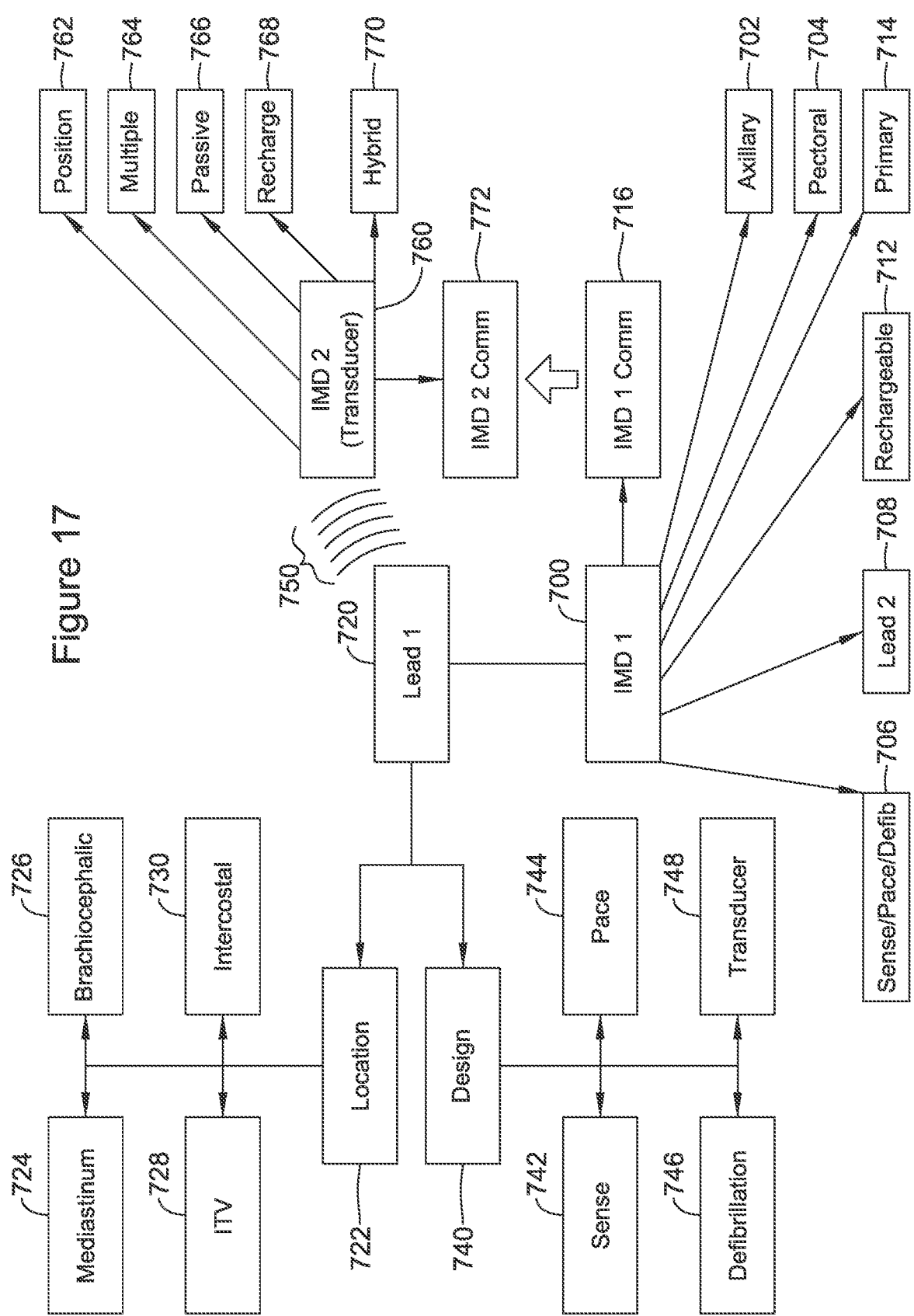
FIG. 17 shows an implantable medical device system in block form.

FIG. 17 shows an implantable medical device system in block form. The figure is designed to illustrate a large number of options and combinations that can be achieved with the present invention.

A system may include a first implantable medical device (IMD), shown at 700, which operates using at least one lead 720, and provides power for use by a second IMD 760. The first IMD 700 may be placed in various suitable locations in the patient including, for example and as shown above, an axillary position 702 (such as in the left axilla and/or near the anterior, mid, or posterior axillary lines) or a pectoral position 704 (such as is in common use for transvenous pacemakers and defibrillators, high on the right or left chest near the clavicle).

The first IMD 700 may include the ability to sense and/or deliver pacing and/or defibrillation therapy, as indicated at 706. For example, the first IMD 700 may have sensing capabilities, including without limitation, the ability to sense arrhythmia, cardiac fusion, cardiac pace capture, asystole, patient activity/motion/posture, surrogates for patient metabolic demand (temperature, blood sugar, motion) or any other desired signal and/or condition. Further the first IMD 700 may include therapy output circuitry to provide pacing or defibrillation therapy. The first IMD 700 may also include the ability to deliver non-electrical therapy such as drug therapy.

The first IMD 700 may include a second lead, as indicated at 708. The first IMD 700 may be a rechargeable device 712, or it may use a primary battery that is non-rechargeable 714. In some examples, the first IMD 700 includes both primary and rechargeable power supplies in which some functions, such as those using the first lead 720 to deliver power to the second IMD 760, are allowed only when sufficient rechargeable power is available, while other functions, such as the ability to sense for arrhythmia and deliver defibrillation therapy, may be available regardless the rechargeable battery status.

The first IMD 700 may also include circuitry to facilitate communication to the second IMD 760 outside of the mechanical signal noted at 750. Such communication may be used to interrogate the second IMD 760 to determine its status, to load program instructions to the second IMD 760, to provide information (such as therapy efficacy) to the second IMD 760, and/or to provide commands to the second IMD 760, as discussed in various embodiments above. For example, the first IMD 700 may command a therapy output by the second IMD, or the first IMD 700 may determine that the second IMD 760 can modify a therapy parameter and may communicate such to the second IMD 760.

The lead 720 may be implanted at a number of locations 722 as indicated above. Example locations may include in the mediastinum 724, in a brachiocephalic vein 726, in the ITV 728, or in an intercostal vein 730. For example, a lead may be implanted in an intercostal vein 730 after accessing the ITV 728 from the brachiocephalic vein (as shown in FIG. 16). In another example, a lead may be implanted in the mediastinum by accessing an intercostal vein 730, for example, in the left axilla or at a location near the sternum, or anywhere therebetween, passing the lead to the ITV 728 from the intercostal vein 730, and then exiting the ITV 728 to enter the mediastinum 724. Mediastinal placement from the ITV is shown, for example, in U.S. patent application Ser. No. 15/814,990, titled TRANSVENOUS MEDIASTINUM ACCESS FOR THE PLACEMENT OF CARDIAC PACING AND DEFIBRILLATION ELECTRODES, and Ser. No. 15/815,051, titled ELECTRODE FOR SENSING, PACING, AND DEFIBRILLATION DEPLOYABLE IN THE MEDIASTINAL SPACE, the disclosures of which are incorporated herein by reference.

The first lead 720 may have a number of design features 740. For example, the lead may include one or more sensing electrodes 742, one or more pacing electrodes 744, one or more defibrillation electrodes 746, and/or one or more transducers 748 that can be used to generate mechanical energy 750, such as an ultrasound output signal. The second lead 708, if provided, may have similar such items.

The first lead 720 is used to generate and transmit a mechanical signal 750, which may be an ultrasound signal, to the second IMB 760. The second IMB 760 includes a transducer to receive the mechanical signal 750.

The second IMD may be implanted in any of the positions 762 noted above. For example, the second IMD may be implanted in one of the chambers of the heart, on the outside of the heart, or within one of the coronary veins or other blood vessels in, on, or adjacent to the heart. There may be multiple second IMDs 760, as indicated at 764.

The second IMD 760 may be a passive device that is responsive to a incoming mechanical signal to deliver therapy, as indicated at 766. In other examples, the second IMD 760 may include a rechargeable 768 power supply, allowing the second IMD to exercise a level of control, which can vary, over its therapy outputs by, for example sensing cardiac signals to configure therapy and/or determine whether and when to deliver therapy. A rechargeable 768 device may receive commands to deliver therapy, or it may determine when to deliver therapy using its own independent control system and/or rules/parameters.

The second IMD 760 may also take the form of a hybrid 770 device having both a primary battery and a rechargeable battery. The functions of a hybrid 770 device may vary in response to the status of the primary and/or rechargeable batteries. For example, the second IMD 760 may be a leadless pacemaker and, if it is a hybrid 770 device, the pacemaker may deliver a life preserving pacing therapy (such as a 30-50 bpm demand pacing output) when operating under only primary cell power, and a more sophisticated pacing output such as a rate adaptive pace therapy or CRT when operating under rechargeable battery power.

The variables and features noted in FIG. 17 are provided for illustrative and non-limiting purposes.

Following is a set of non-limiting examples. Each of these non-limiting examples can stand on its own, or can be combined in various permutations or combinations with one or more of the other examples. The examples comprise references to elements of the drawings associated with the first instance of the use of certain terms, and it should be understood that such references further incorporate the description of the numbered elements provided above.

A first non-limiting example takes the form of an implantable medical device system comprising: a first lead (102, 200, 220, 240, 260, 300, 320, 530, 610, 620, 720) comprising a transducer (104, 152, 206, 226, 242, 262, 264, 302, 332, 536, 612, 614, 616, 622, 624, 626, 640, 748) for converting electrical energy to mechanical energy; an implantable first medical device (100, 150, 500, 600, 700) comprising a canister (502) housing operational circuitry (510, 512, 514, 516, 518, 520, 522) for the implantable first medical device, the implantable first medical device configured to couple to the first lead, the operational circuitry comprising driving means (as described above, an ultrasound driver output may be included in blocks 518, 520, or may be integrated into the first lead 102, 220, 220, 240, 260, 300, 320, 530, 610, 620) for selectively driving the transducer of the first lead; and an implantable second medical device (120, 170, 350, 400, 450, 552, 554, 556, 560, 562, 570, 630, 632, 634, 760) configured for placement in, or on the heart of a patient or in a coronary vein thereof, the implantable second medical device having a receiver means (as described above, a transducer/receiver as shown at 370, 414, 470, 760) for receiving mechanical energy from the transducer (104, 152, 206, 226, 242, 262, 264, 302, 332) and converting received mechanical energy into electrical energy, and a plurality of electrodes (352, 354, 356, 358, 360, 362, 410, 412, 460, 462, 464, 466) for delivering electrical pacing therapy to the heart of a patient; wherein the first lead is configured for placement in an internal thoracic vein (106, 112, 160, 162, 202) of a patient. Insofar as the first lead is configured for placement in an internal thoracic vein, it is meant here that the first lead has an outer diameter, inclusive of the transducer, to facilitate placement of at least a portion thereof in the internal thoracic vein to place the transducer in the same plane as, or beneath, the ribs of the patient.

Additionally or alternatively in or to the first non-limiting example, the first lead comprises a combination transmitter and defibrillation electrode, of which said transducer is a part, wherein the defibrillation electrode is a coil electrode, and the implantable first medical device comprises therapy means for delivering a defibrillation therapy using at least the defibrillation electrode of the first lead.

Additionally or alternatively in or to the first non-limiting example, the first lead comprises a defibrillation electrode, and the implantable first medical device comprises therapy means for delivering a defibrillation therapy using at least the defibrillation electrode of the first lead.

Additionally or alternatively in or to the first non-limiting example, the first lead comprises at least one pacing electrode for outputting pacing therapy.

Additionally or alternatively in or to the first non-limiting example, the first lead comprises a combination transmitter and pacing electrode, of which said transducer is a part.

A second non-limiting example incorporates the first non-limiting example, wherein the first lead comprises a plurality of transducers that are separately addressable by the driver means for separately powering a plurality of implantable second medical devices.

Additionally or alternatively in or to the second non-limiting example, the driver means of the first implantable medical device is configured to separately power the plurality of implantable second medical devices by providing output power via the plurality of transducers at a plurality of different transducer frequencies.

A third non-limiting example incorporates the first and/or second non-limiting examples, wherein the operational circuitry of the implantable first medical device comprises sensing means (such as using sense electrodes 742 and sensing, pacing and defibrillation circuitry 706 in FIG. 17, and/or the combination of I/O circuitry 518 with processing circuitry 510 for analyzing cardiac signals using instructions and parameters selected and set in memory 512 in FIG. 14) for receiving signals from electrodes disposed on the first lead, on a second lead, or on the canister of the first medical device to detect cardiac function.

Additionally or alternatively in or to the third non-limiting example, the operational circuitry comprises therapy determining means coupled to the sensing means for determining whether a pacing therapy delivered by the second implantable medical device has achieved a desirable outcome (such as the combination of I/O circuitry 518 with processing circuitry 510 for analyzing cardiac signals using instructions and parameters selected and set in memory 512 in FIG. 14 to determine therapy results of the therapy delivered by the first medical device using tools and methods as described above, such as those of several related patent applications and concepts described above using one or more of captured cardiac electrical signals, acoustic, motion, or optical sensors), the therapy determining means coupled to adjustment means for adjusting the driver means to increase or decrease an amount of power provided by the driver means to the transducer on the lead (such adjustment means may take the form of a set of instructions in the memory causing the processing circuit 510 to make adjustments to the driver means power level).

Additionally or alternatively in or to the third non-limiting example, the operational circuitry comprises therapy determining means for determining whether a pacing therapy delivered by the second implantable medical device has achieved a desirable outcome (such as the combination of I/O circuitry 518 with processing circuitry 510 for analyzing cardiac signals using instructions and parameters selected and set in memory 512 in FIG. 14 to determine therapy results of the therapy delivered by the first medical device using tools and methods as described above, such as those of several related patent applications and concepts described above using one or more of captured cardiac electrical signals, acoustic, motion, or optical sensors), and adjusting means for adjusting the driver means to modify timing of power provided by the driver means to the transducer on the first lead (such adjustment means may take the form of a set of instructions in the memory causing the processing circuit 510 to make adjustments to the driver means timing characteristics).

Additionally or alternatively in or to any of the first to third non-limiting examples, the transducer of the first lead is an ultrasound transducer.

Additionally or alternatively in or to any of the first to third non-limiting examples, the implantable first medical device operational circuitry is configured to use the driver means to provide power to the second medical device using the transducer on the first lead, and the operational circuitry further comprises control means to modulate an output of the driver circuit to provide a control signal within a power output generated using the transducer (such modulation may be integrated as part of the communication means 522 used to generated and control communication outputs of the device 500).

Additionally or alternatively in or to any of the first to third non-limiting examples, the implantable first medical device operational circuitry is configured to use the driver means to provide power to the second medical device using the transducer on the first lead, and the operational circuitry further comprises: communication means for communicating to the implantable second medical device separate from the transducer of the first lead (such as communication block 522 using conducted communication by way of electrodes 504, 506, 532, 534, and/or 538, or using the antenna 524); and control means to identify and communicate, using the communication means, directions for therapy delivery by the implantable second medical device (such control means may include stored operational instructions in the memory 512 for execution by the processing block 510 controlling the communication block 522).

Additionally or alternatively in or to any of the first to third non-limiting examples, the system comprises a second lead, wherein the implantable first medical device comprises a header (526) adapted to receive each of the first and second leads, and further wherein the second lead comprises a transducer for converting electrical energy to mechanical energy, and the driver means is configured to selectively drive the transducer of the first lead and the second lead separately.

Additionally or alternatively in or to any of the first to third non-limiting examples, the implantable second medical device may comprise a rechargeable battery or capacitor (noted at 372, 472, and 768)coupled to the receiver means thereof to receive and store energy received from the transducer of the first lead.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device system comprising:
a first lead comprising a transducer for converting electrical energy to mechanical energy;
an implantable first medical device comprising a canister housing operational circuitry for the implantable first medical device, the implantable first medical device configured to couple to the first lead, the operational circuitry including driver circuitry for selectively driving the transducer of the lead; and
an implantable second medical device configured for placement in the heart of a patient having a receiver for receiving mechanical energy from the transducer and converting received mechanical energy into electrical energy, and a plurality of electrodes for delivering electrical pacing therapy to the heart of a patient;
wherein the first lead is configured for placement in an internal thoracic vein of a patient such that the transducer resides within the internal thoracic vein.

2. The system of claim 1 wherein the first lead comprises a defibrillation electrode, and the implantable first medical device comprises therapy circuitry for delivering a defibrillation therapy using at least the defibrillation electrode of the first lead.

3. The system of claim 1 wherein the first lead comprises at least one pacing electrode for outputting pacing therapy.

4. The system of claim 1 wherein the first lead comprises a plurality of transducers that are separately addressable by the driver circuitry for separately powering a plurality of implantable second medical devices.

5. The system of claim 4 wherein the first implantable medical device is configured to separately power the plurality of implantable second medical devices by providing output power via the plurality of transducers at a plurality of different transducer frequencies.

6. The system of claim 1 wherein the operational circuitry of the implantable first medical device comprises sensing circuitry for receiving signals from electrodes disposed on the first lead, on a second lead, or on the canister of the first medical device to detect cardiac function.

7. The system of claim 6 wherein the operational circuitry is configured to use the sensing circuitry to determine whether a pacing therapy delivered by the second implantable medical device has achieved a desirable outcome, and to adjust the driver circuitry to increase or decrease an amount of power provided by the driver circuitry to the transducer on the lead.

8. The system of claim 6 wherein the operational circuitry is configured to use the sensing circuitry to determine whether a pacing therapy delivered by the second implantable medical device has achieved a desirable outcome, and to adjust the driver circuitry to modify timing of power provided by the driver circuitry to the transducer on the first lead.

9. A system as in claim 1 wherein the implantable first medical device is configured to power and control therapy delivery by the implantable second medical device by:
providing power to the second medical device using the transducer on the first lead; and
controlling operation of the second medical device by providing a control signal within a power output generated using the transducer.

10. A system as in claim 1 further comprising a second lead, wherein the implantable first medical device comprises a header adapted to receive each of the first and second leads, and further wherein the second lead comprises a transducer for converting electrical energy to mechanical energy, and the driver circuitry is configured to selectively drive the transducer of the first lead and the second lead separately.

11. The system of claim 1 wherein the canister is adapted for placement in the left axilla of the patient, having a generally rectangular shape.

12. The system of claim 1 wherein the canister is adapted for placement near the left clavicle of the patient, having a generally rectangular shape.

13. A method of treating a patient comprising:
generating mechanical energy using a first transducer located on a lead, wherein at least a portion of the lead is located in an internal thoracic vein of the patient;
receiving the mechanical energy at a second transducer on an implantable pacemaker located in or on the heart of the patient;
converting the mechanical energy to electrical energy in the implantable pacemaker; and
generating a therapy output using the electrical energy with the implantable pacemaker.

14. The method of claim 13 wherein the lead is coupled to an implantable defibrillator comprising a housing containing one or more batteries, sensing circuitry, therapy delivery circuitry, and a driver for the transducer, the lead further including a defibrillation coil electrode coupled to therapy delivery circuitry located in the housing such that the subcutaneous defibrillator is configured to:

deliver defibrillation therapy using the housing and the defibrillation coil in a shocking configuration; and provide power to the leadless pacemaker using the driver and the transducer on the lead.

15. The system of claim 14 wherein the housing is located subcutaneously.

16. The method of claim 13 wherein the lead is coupled to an implantable cardiac device comprising a housing containing one or more batteries, sensing circuitry, and a driver for the transducer, such that the implantable cardiac device is configured to:

provide power to the leadless pacemaker using the driver and the transducer on the lead; and use the sensing circuitry to determine one or more of an effectiveness of the leadless pacemaker output, a patient cardiac state, or a patient activity level.

17. The system of claim 16 wherein the housing is located subcutaneously.

18. The method of claim 13 wherein the first transducer is located in the mediastinal space.

19. The method of claim 13 wherein the first transducer is located in an intercostal vein connected to the internal thoracic vein.

20. The method of claim 13 wherein the first transducer is located in the internal thoracic vein.

* * * * *